(12) United States Patent
Murayama et al.

(10) Patent No.: US 12,383,195 B2
(45) Date of Patent: Aug. 12, 2025

(54) PHYSIOLOGICAL INFORMATION PROCESSING APPARATUS, PHYSIOLOGICAL INFORMATION PROCESSING METHOD AND STORAGE MEDIUM

(71) Applicant: NIHON KOHDEN CORPORATION, Tokyo (JP)

(72) Inventors: Yoshinori Murayama, Tokorozawa (JP); Osamu Nagata, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 1152 days.

(21) Appl. No.: 17/214,305

(22) Filed: Mar. 26, 2021

(65) Prior Publication Data
US 2022/0218275 A1    Jul. 14, 2022

(30) Foreign Application Priority Data
Jan. 12, 2021    (JP) .................. 2021-002909

(51) Int. Cl.
*A61B 5/00* (2006.01)
*A61B 5/02* (2006.01)
(Continued)

(52) U.S. Cl.
CPC .......... *A61B 5/4821* (2013.01); *A61B 5/0205* (2013.01); *A61B 5/021* (2013.01);
(Continued)

(58) Field of Classification Search
None
See application file for complete search history.

(56) References Cited

U.S. PATENT DOCUMENTS

2002/0017296 A1* 2/2002 Hickle ................. A61B 5/4821
128/204.23
2003/0055343 A1* 3/2003 Korhonen ............ A61B 5/4821
600/509
(Continued)

FOREIGN PATENT DOCUMENTS

JP           4980215 B2    7/2012
WO    2017/145715 A1    8/2017

OTHER PUBLICATIONS

Joosten et al. Anesthetic Management Using Multiple Closed-loop Systems and Delayed Neurocognitive Recovery. Anesthesiology, vol. 13, No. 2, Feb. 2020. (Year: 2020).*
(Continued)

*Primary Examiner* — Etsub D Berhanu
(74) *Attorney, Agent, or Firm* — Sughrue Mion, PLLC

(57) ABSTRACT

A physiological information processing apparatus includes a processor and a memory configured to store a computer readable command. The computer readable command is executed by the processor, the physiological information processing apparatus is configured to acquire physiological information data of a subject to which an anesthetic is administered, specify, based on the physiological information data, at least one of an appropriate management time, which is a time during which anesthesia management is appropriately performed on the subject, and an inappropriate management time, which is a time during which the anesthesia management is not appropriately performed, calculate an anesthesia management evaluation index, which is an evaluation index for the anesthesia management, based on the at least one of the inappropriate management time and the appropriate management time and an operation time of the subject, and output the calculated anesthesia management evaluation index.

15 Claims, 14 Drawing Sheets

(51) Int. Cl.
  *A61B 5/0205* (2006.01)
  *A61B 5/021* (2006.01)
  *A61B 5/024* (2006.01)
  *A61B 5/369* (2021.01)
  *A61B 5/372* (2021.01)

(52) U.S. Cl.
  CPC .............. *A61B 5/024* (2013.01); *A61B 5/369* (2021.01); *A61B 2505/05* (2013.01)

(56) References Cited

U.S. PATENT DOCUMENTS

| | | | |
|---|---|---|---|
| 2005/0042280 A1* | 2/2005 | Rogers | A61K 47/20 514/474 |
| 2006/0009733 A1 | 1/2006 | Martin | |
| 2009/0118697 A1 | 5/2009 | Martin | |
| 2011/0137297 A1* | 6/2011 | Kiani | A61B 5/1455 604/890.1 |
| 2015/0224114 A1* | 8/2015 | Kondo | A61K 31/58 540/562 |
| 2016/0175522 A1 | 6/2016 | Martin | |
| 2017/0124273 A1* | 5/2017 | Huang | A61B 5/742 |

OTHER PUBLICATIONS

Ramsay et al. Controlled Sedation with Alphaxalone-Alphadolone. British Medical Journal, Jun. 22, 1974. (Year: 1974).*
Kadry et al. Anesthesia Information Management Systems: Past, Present, and Future of Anesthesia Records. Mount Sinai Journal of Medicine, 79:154-165, 2012. (Year: 2012).*
Mason et al. Total Intravenous Anaesthesia With an Integrated Computer Control System. IFAC Proceedings vols. vol. 30, Issue 2, Mar. 1997, pp. 205-207. (Year: 1997).*
Extended European Search Report dated Sep. 9, 2021, issued by the European Patent Office in counterpart European patent Application No. 21165910.7.

* cited by examiner

PHYSIOLOGICAL INFORMATION PROCESSING APPARATUS, PHYSIOLOGICAL INFORMATION PROCESSING METHOD AND STORAGE MEDIUM

CROSS-REFERENCE TO RELATED APPLICATION

This application claims priority from Japanese Patent Application No. 2021-002909, filed on Jan. 12, 2021, the entire subject matter of which is incorporated herein by reference.

TECHNICAL FIELD

The present disclosure relates to a physiological information processing apparatus and a physiological information processing method. Further, the present disclosure relates to a program configured to cause a computer to execute the physiological information processing method and a computer-readable storage medium in which the program is stored.

BACKGROUND

During an operation, appropriate anesthesia management is an important matter for a patient who receives the operation under general anesthesia and a doctor who performs the operation. The appropriate anesthesia management for the patient is achieved by three types of management including appropriate sedative management, appropriate analgesic management, and appropriate muscle relaxation management. Here, the anesthesia management is a generic concept of the sedative management, the analgesic management, and the muscle relaxation management. An anesthetist who performs the anesthesia management selects an optimal anesthetic based on physiological information data of the patient, and then carefully administers the anesthetic based on own operational experience while observing a vital reaction of the patient.

Meanwhile, there is also an automatic anesthesia management system that automates administration of an anesthetic based on a BIS value, which is an anesthesia depth index value of a patient. For example, Japanese Patent No. 4980215 discloses a medicament delivery device which includes an automatic response monitoring system that monitors a response of a patient, a monitoring device that monitors a BIS value of the patient, and a sedative injector.

SUMMARY

During manual anesthesia management performed by an anesthetist, the anesthetist performs subjective anesthesia management based on own experience while observing a vital reaction of a patient. Therefore, there is no mechanism for objectively evaluating the anesthesia management performed by the anesthetist. The automatic anesthesia management system as disclosed in Japanese Patent No. 4980215 also does not include any mechanism for objectively evaluating skillfulness of automatic anesthesia management. As described above, there is room for considering a system capable of objectively digitalizing and visualizing the skillfulness of the anesthesia management.

An object of the present disclosure is to provide a physiological information processing apparatus and a physiological information processing method capable of objectively digitalizing and visualizing the skillfulness of the anesthesia management.

A physiological information processing apparatus according to a first aspect of the present disclosure can include a processor and a memory configured to store a computer readable command. The computer readable command is executed by the processor, the physiological information processing apparatus is configured to: acquire physiological information data of a subject to which an anesthetic is administered, specify, based on the physiological information data, at least one of an appropriate management time, which is a time during which anesthesia management is appropriately performed on the subject, and an inappropriate management time, which is a time during which the anesthesia management is not appropriately performed, calculate an anesthesia management evaluation index, which is an evaluation index for the anesthesia management, based on the at least one of the inappropriate management time and the appropriate management time and an operation time of the subject, and output the calculated anesthesia management evaluation index.

According to the above configuration, after the at least one of the appropriate management time and the inappropriate management time are specified based on the physiological information data, the anesthesia management evaluation index is calculated and output based on the at least one of the appropriate management time and the inappropriate management time and the operation time. In this way, the skillfulness of the anesthesia management can be objectively digitalized and visualized by the calculated anesthesia management evaluation index.

A physiological information processing apparatus according to a second aspect of the present disclosure can include a processor and a memory configured to store a computer readable command. When the computer readable command is executed by the processor, the physiological information processing apparatus is configured to:

acquire electroencephalogram data of a subject to which an anesthetic is administered, specify, based on the electroencephalogram data, a first appropriate management time, which is a time during which sedative management is appropriately performed on the subject, and a first inappropriate management time, which is a time during which the sedative management is not appropriately performed, acquire pain reaction data indicating a pain reaction of the subject, specify, based on the pain reaction data, a second appropriate management time, which is a time during which analgesic management is appropriately performed on the subject, and a second inappropriate management time, which is a time during which the analgesic management is not appropriately performed, acquire stimulus-response data indicating a stimulus-response of the subject, specify, based on the stimulus-response data, a third appropriate management time, which is a time during which muscle relaxation management is appropriately performed on the subject, and a third inappropriate management time, which is a time during which the muscle relaxation management is not appropriately performed, calculate, based on the first to third inappropriate management times and an operation time of the subject, a comprehensive anesthesia management evaluation index, which is a comprehensive evaluation index for anesthesia management of the subject, and output the calculated anesthesia management evaluation index.

According to the above configuration, the first inappropriate management time, which is the time during which the sedative management is not appropriately performed, is specified based on the electroencephalogram data. The second inappropriate management time, which is the time during which the analgesic management is not appropriately performed, is specified based on the pain reaction data, and the third inappropriate management time, which is the time during which the muscle relaxation management is not appropriately performed, is specified based on the stimulus-response data. Thereafter, the comprehensive anesthesia management evaluation index is calculated and output based on the first to third inappropriate management times and the operation time. As described above, the skillfulness of the anesthesia management can be comprehensively and objectively digitalized and visualized through the comprehensive anesthesia management evaluation index that is a comprehensive evaluation index calculated based on the three pieces of physiological information data indicating sedative, analgesia, and muscle relaxation.

A physiological information processing method according to a third aspect of the present disclosure is executed by a computer and can include acquiring physiological information data of a subject to which an anesthetic is administered;

specifying, based on the physiological information data, at least one of an appropriate management time, which is a time during which anesthesia management is appropriately performed on the subject, and an inappropriate management time, which is a time during which the anesthesia management is not appropriately performed;

calculating an anesthesia management evaluation index, which is an evaluation index for the anesthesia management, based on the at least one of the inappropriate management time and the appropriate management time and an operation time of the subject; and outputting the calculated anesthesia management evaluation index.

According to the above method, after the at least one of the appropriate management time and the inappropriate management time are specified based on the physiological information data, the anesthesia management evaluation index is calculated and output based on the at least one of the appropriate management time and the inappropriate management time and the operation time. In this way, the skillfulness of the anesthesia management can be objectively digitalized and visualized by the calculated anesthesia management evaluation index.

A physiological information processing method according to a fourth aspect of the present disclosure is executed by a computer and can include acquiring electroencephalogram data of a subject to which an anesthetic is administered;

specifying, based on the electroencephalogram data, a first appropriate management time, which is a time during which sedative management is appropriately performed on the subject, and a first inappropriate management time, which is a time during which the sedative management is not appropriately performed;

acquiring pain reaction data indicating a pain reaction of the subject;

specifying, based on the pain reaction data, a second appropriate management time, which is a time during which analgesic management is appropriately performed on the subject, and a second inappropriate management time, which is a time during which the analgesic management is not appropriately performed;

acquiring stimulus-response data indicating a stimulus-response of the subject; specifying, based on the stimulus-response data, a third appropriate management time, which is a time during which muscle relaxation management is appropriately performed on the subject, and a third inappropriate management time, which is a time during which the muscle relaxation management is not appropriately performed;

calculating, based on the first to third inappropriate management times and an operation time of the subject, a comprehensive anesthesia management evaluation index, which is a comprehensive evaluation index for anesthesia management of the subject, and outputting the calculated anesthesia management evaluation index.

According to the above method, the first inappropriate management time, which is the time during which the sedative management is not appropriately performed, is specified based on the electroencephalogram data. The second inappropriate management time, which is the time during which the analgesic management is not appropriately performed, is specified based on the pain reaction data, and the third inappropriate management time, which is the time during which the muscle relaxation management is not appropriately performed, is specified based on the stimulus-response data. Thereafter, the comprehensive anesthesia management evaluation index is calculated and output based on the first to third inappropriate management times and the operation time. As described above, the skillfulness of the anesthesia management can be comprehensively and objectively digitalized and visualized through the comprehensive anesthesia management evaluation index that is the comprehensive evaluation index calculated based on the three pieces of physiological information data indicating sedative, analgesia, and muscle relaxation.

A program configured to cause a computer to execute the physiological information processing methods may also be provided. Further, a computer-readable medium in which the program is stored may be provided.

According to the present disclosure, the physiological information processing apparatus and the physiological information processing method capable of objectively digitalizing and visualizing the skillfulness of the anesthesia management can be provided.

DETAILED DESCRIPTION

Hereinafter, the present embodiment will be described with reference to the drawings.

Figure 1:
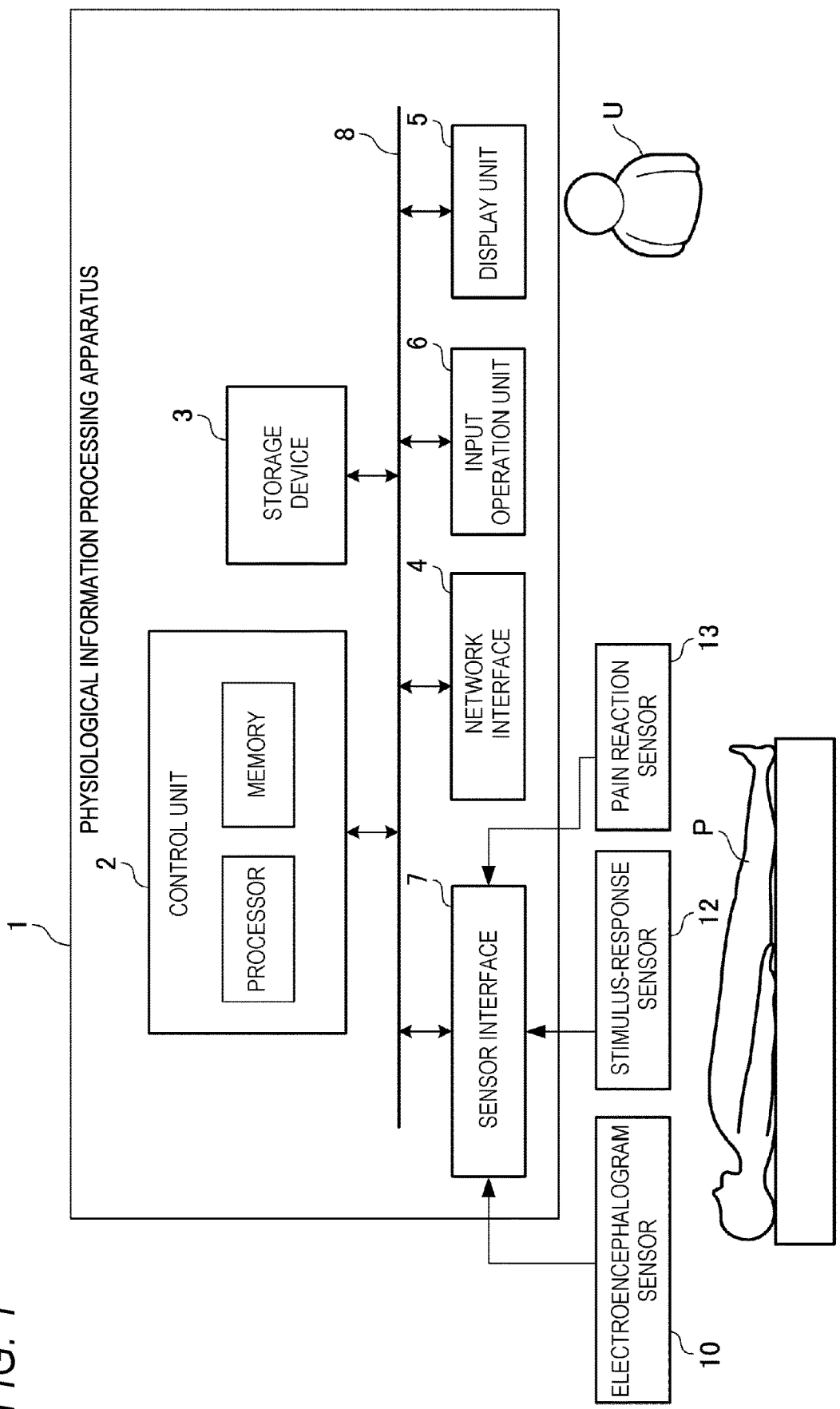
FIG. 1 is a block diagram illustrating a configuration of a physiological information processing apparatus according to an embodiment of the presently disclosed subject matter (hereinafter referred to as the present embodiment).

FIG. 1 is a block diagram illustrating a configuration of a physiological information processing apparatus 1 according to the present embodiment. As illustrated in FIG. 1, the physiological information processing apparatus 1 (hereinafter, simply referred to as "processing apparatus 1") can include a control unit 2, a storage device 3, a network interface 4, a display unit 5, an input operation unit 6, and a sensor interface 7. Such components are connected to each other via a bus 8 so as to be capable of communicating with each other.

The processing apparatus 1 may be a dedicated medical device (for example, a patient monitor) configured to display physiological information of a patient P (subject), or may be, for example, a personal computer, a work station, a smartphone, or a tablet computer.

The control unit 2 can include one or more memories and one or more processors. The one or more memories are non-transitory computer-readable mediums configured to store computer readable commands (programs). For example, the one or more memories may each be configured with a read-only memory (ROM) in which various programs and the like are stored, and a random access memory (RAM) including a plurality of work areas in which various programs and the like executed by the one or more processors are stored. The ROM may be configured by a flash memory or the like. The one or more processors can include, for example, a central processing unit (CPU), a micro processing unit (MPU), and/or a graphics processing unit (GPU). The CPU may be configured by a plurality of CPU cores. The GPU may be configured by a plurality of GPU cores. The one or more processors may be configured to load a program specified from various programs incorporated in the storage device 3 or the ROM onto the RAM and execute various processes in cooperation with the RAM.

In particular, the one or more processors may load a physiological information processing program to be described later below onto the RAM and execute the program in cooperation with the RAM such that the control unit 2 may control various operations of the processing apparatus 1. Details of the physiological information processing program will be described later below.

The storage device 3 is a non-transitory computer-readable medium, for example, a storage device (storage) such as a hard disk drive (HDD), a solid state drive (SSD), or a flash memory, and is configured to store programs and various types of data. The physiological information processing program may be incorporated in the storage device 3. The storage device 3 may also store physiological information data (for example, electroencephalogram data, a TOF count value, and heart rate data) indicating physiological information of the patient P (subject) and information on an anesthesia management evaluation index (for example, a sedative management evaluation index value). For example, the physiological information data may be stored, via the sensor interface 7, in the storage device 3 from various sensors (an electroencephalogram sensor and the like) connected to the processing apparatus 1.

The network interface 4 is configured to connect the processing apparatus 1 to a communication network. Specifically, the network interface 4 may include various wired connection terminals configured to communicate with an external device such as a server via the communication network. The network interface 4 may include a wireless communication module configured to perform wireless communication with the external device. A wireless communication standard between the external device and the processing apparatus 1 is Wi-Fi (registered trademark), Bluetooth (registered trademark), ZigBee (registered trademark), or LPWA. The communication network is a local area network (LAN), a wide area network (WAN), the Internet, or the like. For example, the physiological information processing program and the physiological information data of the patient may be acquired from a server arranged on the communication network via the network interface 4.

The display unit 5 may be a liquid crystal display or an organic EL display, or may be a transmissive or non-transmissive head mount display mounted on a head portion of an operator U (medical worker). Further, the display unit 5 may also be a projector device that projects image data onto a screen. It should be noted that the processing apparatus 1 may not include the display unit 5. In this case, image data output from the processing apparatus 1 may be displayed on a display unit of an external device such as a central monitor via the network interface 4 or an image interface (not illustrated).

The input operation unit 6 is configured to receive an input operation of the operator U who operates the processing apparatus 1 and to generate an instruction signal corresponding to the input operation. The input operation unit 6 is, for example, a touch panel overlaid on the display unit 5, an operation button provided on a housing of the processing apparatus 1, or a mouse and/or a keyboard connected to an input and output interface (for example, a USB interface which is not illustrated). After the instruction signal generated by the input operation unit 6 is transmitted to the control unit 2 via the bus 8, the control unit 2 performs a predetermined operation in accordance with the instruction signal.

The sensor interface 7 is an interface configured to connect the various sensors to the processing apparatus 1.

The sensor interface 7 is connected to each of an electroencephalogram sensor 10, a stimulus-response sensor 12, and a pain reaction sensor 13. The sensor interface 7 may include an analog processing circuit configured to process signals output from the various sensors. The analog processing circuit may include, for example, a filter circuit, an amplifier, and an A/D converter. The physiological information data, (digital data) such as electroencephalogram data output from the sensor interface 7 is transmitted to the control unit 2. Thereafter, the control unit 2 performs a predetermined calculation relative to the received physiological information data.

The electroencephalogram sensor 10 is mounted on a head portion of the patient P, and is configured to acquire the electroencephalogram data which indicates an electroencephalogram of the patient P. The electroencephalogram data output from the electroencephalogram sensor 10 is transmitted to the control unit 2 via the sensor interface 7. Thereafter, the control unit 2 may calculate various parameters (for example, a BIS value and an SQI value) related to the electroencephalograms based on the transmitted electroencephalogram data. The electroencephalogram sensor 10 may also be configured as a BIS monitor. In this case, the electroencephalogram sensor 10 may transmit the electroencephalogram data and the parameters (the BIS value and the SQI value) calculated based on the electroencephalogram data to the control unit 2.

The bispectral index (BIS) value is an index which indicating a sedative effect of the patient P provided by a sedative (for example, propofol). The BIS value is a value between 0 and 100. As the BIS value decreases, a consciousness level of the patient P decreases (an anesthesia depth increases). When determining whether a degree of sedative of the patient is appropriate, 40 to 60 is an appropriate range of the BIS value. However, in the present embodiment, it is determined that the degree of sedative (anesthesia depth) of the patient P during an operation is appropriate when the BIS value is 35 to 55. The signal quality index (SQI) value is an index indicating a proportion of reliable electroencephalogram data among electroencephalogram data obtained during past 60 seconds. As the SQI value increases, quality of the electroencephalogram data increases, whereas the quality of the electroencephalogram data decreases as the SQI value decreases. 50% or more is a reliable value of the SOT value. In the present embodiment, when the SQI value is 80% or more, it is determined that the quality of the electroencephalogram data and reliability of the BIS value are high.

The stimulus-response sensor 12 is a muscle relaxation module that is attached to a wrist and a finger of the patient P and is configured to apply a stimulation current to the patient P so as to acquire stimulus-response data (for example, a TOF ratio or a TOF count value) indicating a stimulus-response of the patient P in response to the stimulation current. The stimulus-response sensor 12 may apply, to the patient P, a train-of-four (TOF) stimulation during which four continuous stimulation currents are applied to the patient at intervals of 0.5 seconds. In this case, the TOF stimulation is applied to the patient P at intervals of 15 seconds. The TOF ratio indicates a ratio of a thumb stimulus-response in response to a first electric stimulation T1 to the thumb stimulus-response in response to a fourth electric stimulation T4 during the TOF stimulation (T4/T1). In the present embodiment, when the TOF ratio is in a range of 1%≤TOF ratio 10%, it is determined that muscle relaxation management of the patient P is appropriate.

The TOF count value indicates the number of times of stimulus-responses of the patient in response to the four continuous stimulation currents. For example, when there are four times of stimulus-responses of the patient in response to the four continuous stimulation currents, the TOF count value is 4. When there is one stimulus-response of the patient in response to the four continuous stimulation currents, the TOF count value is 1. In the present embodiment, when the TOF count value is 1, it is determined that the muscle relaxation management of the patient P is appropriate. The stimulus-response sensor 12 transmits the stimulus-response data such as the TOF count value to the control unit 2 via the sensor interface 7. Although the stimulus-response sensor 12 applies the stimulation current to the patient P in the TOF mode in the present embodiment, the stimulation current may also be applied to the patient P in a mode other than the TOF mode (for example, in a tetanus stimulation (TET) mode).

The pain reaction sensor 13 is mounted on the patient P, and is configured to acquire pain reaction data indicating a pain reaction of the patient P. The pain reaction sensor 13 may be, for example, a pulse wave sensor that acquires pulse wave data indicating a change over time in a pulse wave of the patient P or an electrocardiogram sensor that acquires electrocardiogram data indicating a change over time in an electrocardiogram of the patient P. The pain reaction sensor 13 may also be a blood pressure sensor that acquires blood pressure data indicating a change over time in blood pressure (systolic blood pressure or diastolic blood pressure) of the patient P. In the present embodiment, the pain reaction data includes at least one of heart rate data and blood pressure data. That is, in the present embodiment, whether analgesic management of the patient P is appropriate is determined based on the heart rate data and/or the blood pressure data. The pain reaction sensor 13 includes at least one of the pulse wave sensor, the electrocardiogram sensor, and the blood pressure sensor. The pain reaction sensor 13 transmits the pain reaction data to the control unit 2 via the sensor interface 7.

Figure 2:
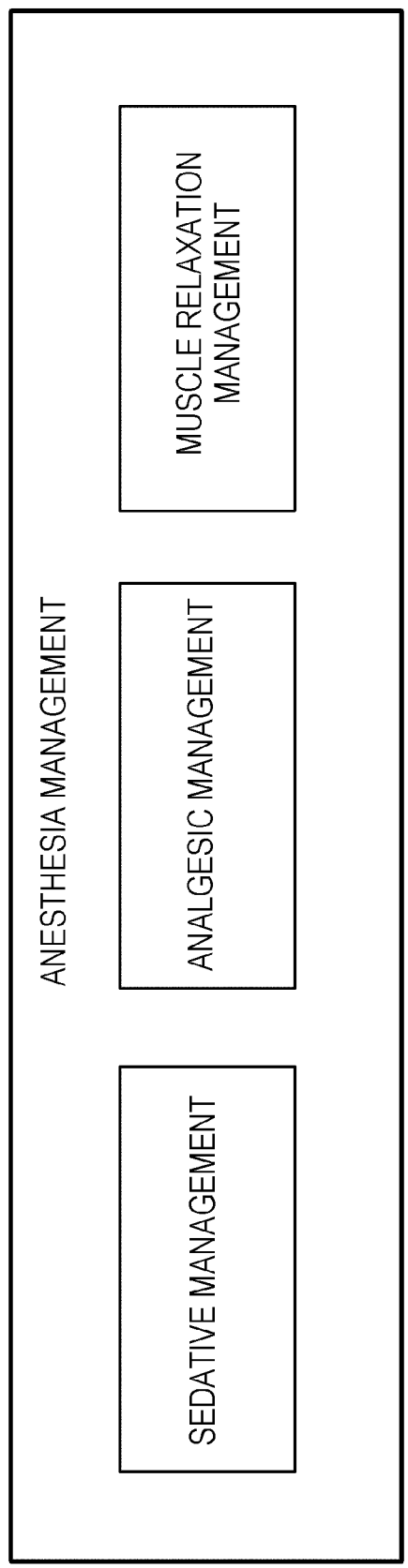
FIG. 2 illustrates details of anesthesia management.

As illustrated in FIG. 2, anesthesia management is achieved by three types of management including the sedative management, the analgesic management, and the muscle relaxation management. In the present embodiment, the sedative management, the analgesic management, and the muscle relaxation management correspond to specific concepts of the anesthesia management. Further, in the present embodiment, an sedative management evaluation index that is an evaluation index for the sedative management, a muscle relaxation management evaluation index that is an evaluation index for the muscle relaxation management, and an analgesic management evaluation index that is an evaluation index for the analgesic management correspond to specific concepts of an anesthesia management evaluation index that is an evaluation index for the anesthesia management. As will be described later below, a comprehensive anesthesia management evaluation index, which is a comprehensive evaluation index for the anesthesia management, is calculated based on parameters related to the sedative management, parameters related to the analgesic management, and parameters related to the muscle relaxation management.

In the present embodiment, a sedative (for example, propofol), an analgesic (for example, remifentanil), and a muscle relaxant (for example, rocuronium) are used as anesthetics to be administered to the patient P during an operation.

Hereinafter, methods of calculating the sedative management evaluation index, the muscle relaxation management evaluation index, and the analgesic management evaluation index as evaluation indexes of the anesthesia management for the patient P during the operation will be described.
(Sedative Management Evaluation Index)

Figure 3:
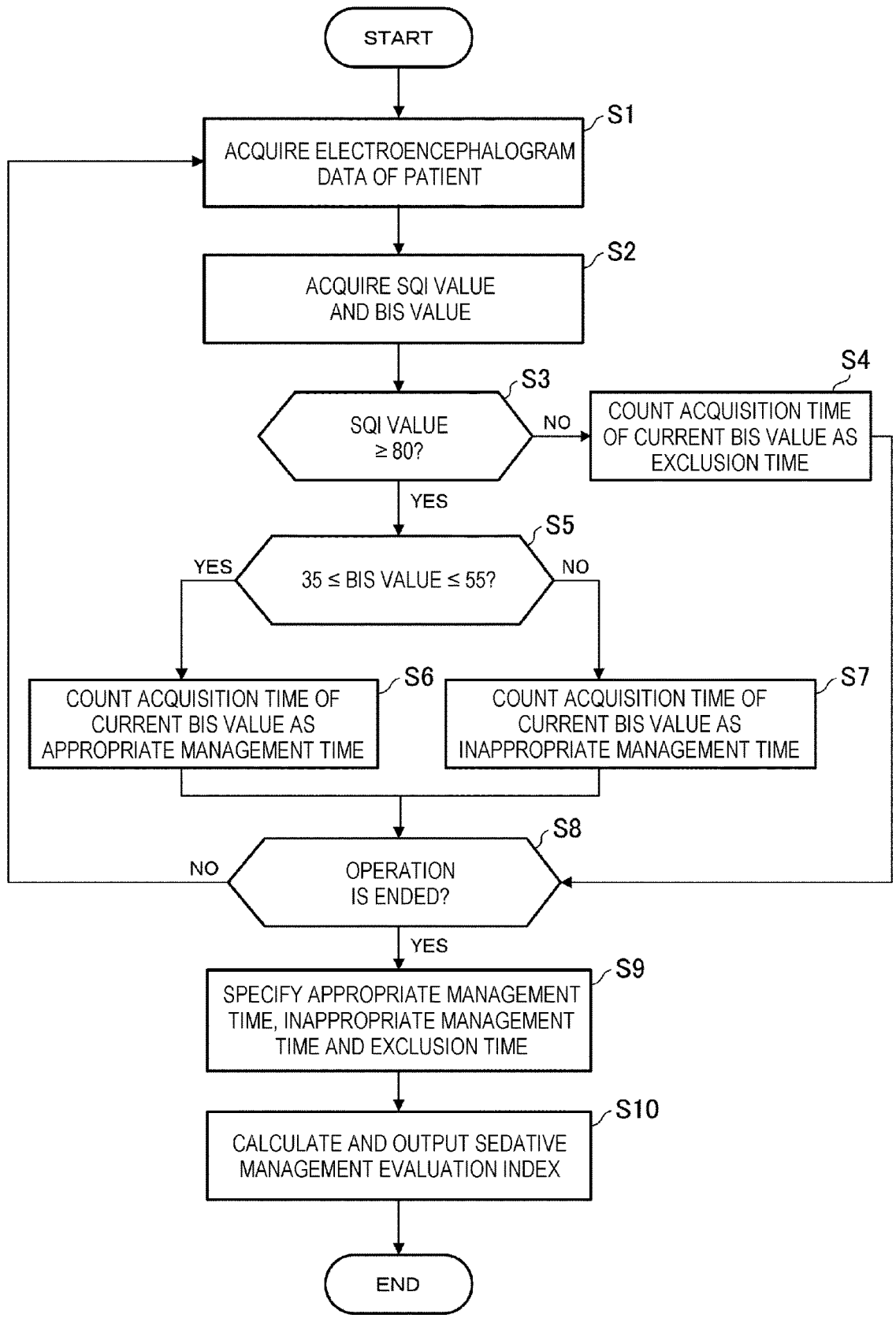
FIG. 3 is a flowchart illustrating a method of calculating a sedative management evaluation index.

First, the method of calculating the sedative management evaluation index, which is the evaluation index for the sedative management of the patient P to which the sedative is administered, will be described below with reference to FIG. 3. FIG. 3 is a flowchart illustrating the method of calculating the sedative management evaluation index.

As illustrated in FIG. 3, in step S1, when the operation of the patient P to which the sedative is administered is started, the control unit 2 acquires the electroencephalogram data indicating the electroencephalogram of the patient P from the electroencephalogram sensor 10. Next, based on the acquired electroencephalogram data, the control unit 2 acquires the BIS value and the SQI value based on the electroencephalogram data (step S2). The BIS value and the SQI value are examples of the physiological information data. When the electroencephalogram sensor 10 is an electroencephalogram monitor, the electroencephalogram sensor 10 may specify the BIS value and the SOI value based on the electroencephalogram data, and then transmit the BIS value and the SQI value to the control unit 2.

Next, the control unit 2 determines whether the SQI value is 80% or more (step S3), When the SQI value is less than 80% (NO in step S3), the control unit 2 determines that the quality of the electroencephalogram data and the reliability of the BIS value are low, and then counts an acquisition time of the current BIS value as an exclusion time (step S4). The term "exclusion time" as used herein refers to a time to be subtracted from an operation time from a start of the operation to an end of the operation. When the sedative management evaluation index to be described later below is calculated, the sedative management evaluation index can be calculated in accordance with skillfulness of the actual sedative management by subtracting the exclusion time from the operation time. On the other hand, when the SQI value is equal to or higher than 80% (YES in step S3), the control unit 2 determines that the quality of the electroencephalogram data and the reliability of the BIS value are high, and then proceeds to the process of step S5.

In step S5, the control unit 2 determines whether the BIS value satisfies a condition of 35≤BIS value≤55 (an example of a second condition). When the BIS value is included in the range of 35 to 55 (YES in step S5), the control unit 2 determines that the degree of sedative of the patient P is appropriate, and then counts an acquisition time of the current BIS value as an appropriate management time (step S6). The term "appropriate management time" as used herein refers to a time when the sedative management is appropriately performed on the patient P, On the other hand, when the BIS value is not included in the range of 35 to 55 (NO in step S5), the control unit 2 determines that the degree of sedative of the patient P is not appropriate, and then counts an acquisition time of the current BIS value as an inappropriate management time (step S7). The term "inappropriate management time" as used herein refers to a time when the sedative management is not appropriately performed on the patient P.

Next, when the operation of the patient P is not ended (NO in step S8), the processes of steps S1 to S7 are repeatedly performed. For example, when the BIS value is updated every 15 seconds, the processes of steps S1 to S7 may be repeatedly performed every 15 seconds. In this case, the acquisition time of the current BIS value (15 seconds), which is a time from timing when a previous BIS value is acquired to timing when the current BIS value is acquired, is counted as the appropriate management time, the inappropriate management time, or the exclusion time. On the other hand, when the operation of the patient P is ended (YES in step S8), the process proceeds to step S9.

Next, the control unit 2 specifies the appropriate management time, the inappropriate management time, and the exclusion time counted during the operation time (step S9). Thereafter, the control unit 2 calculates a sedative management evaluation index Ps based on the operation time, the appropriate management time, and the exclusion time (step S10). For example, the sedative management evaluation index Ps may be calculated based on the following formula (1).

$$Ps = Tr1/(T0-Te1) \times 100\% \tag{1}$$

Here, Tr1 refers to the appropriate management time, T0 refers to the operation time, and Te1 refers to the exclusion time. For example, in a case where the operation time T0 is 300 minutes, the exclusion time Te1 is 20 minutes, and the appropriate management time Tr1 is 250 minutes, the sedative management evaluation index Ps is about 89%.

Thereafter, the control unit 2 outputs the calculated sedative management evaluation index Ps. For example, the control unit 2 may display information on the sedative management evaluation index Ps on the display unit 5. In particular, the control unit 2 may display the information on the sedative management evaluation index Ps on a display screen on which information on the electroencephalogram data (for example, an electroencephalogram waveform or the BIS value) is displayed. Further, the control unit 2 may store the information on the sedative management evaluation index Ps in the storage device 3 in a state of being associated with information on the operation of the patient P.

According to the present embodiment, after the appropriate management time, the inappropriate management time, and the exclusion time are specified based on the BIS value and the SQI value, the sedative management evaluation index Ps is calculated based on the operation time T0, the appropriate management time Tr1, and the exclusion time Te1, and then the sedative management evaluation index Ps is output. In this way, it is possible to objectively digitalize and visualize skillfulness of the sedative management based on the sedative management evaluation index Ps. By presenting the information on the sedative management evaluation index Ps to an anesthetist who is in charge of the operation of the patient P, the anesthetist can know an objective evaluation of the sedative management. Further, when the anesthesia management of the patient P is performed by an automatic anesthesia management system, it is possible to objectively evaluate the skillfulness of the sedative management performed by the automatic anesthesia management system through the sedative management evaluation index Ps.

Although the sedative management evaluation index Ps is output when the operation of the patient P is ended in the present embodiment, the sedative management evaluation index Ps may also be output during the operation of the patient P. In this case, the sedative management evaluation index Ps may be sequentially updated along with a progress of the operation. When the sedative management evaluation index Ps is output during the operation of the patient P, the operation time T0 is a time from an operation start time is to a current time tc. At this time, the determination in step S8 of the control unit 2 may be performed after step S10.

(Muscle Relaxation Management Evaluation Index)

Figure 4:
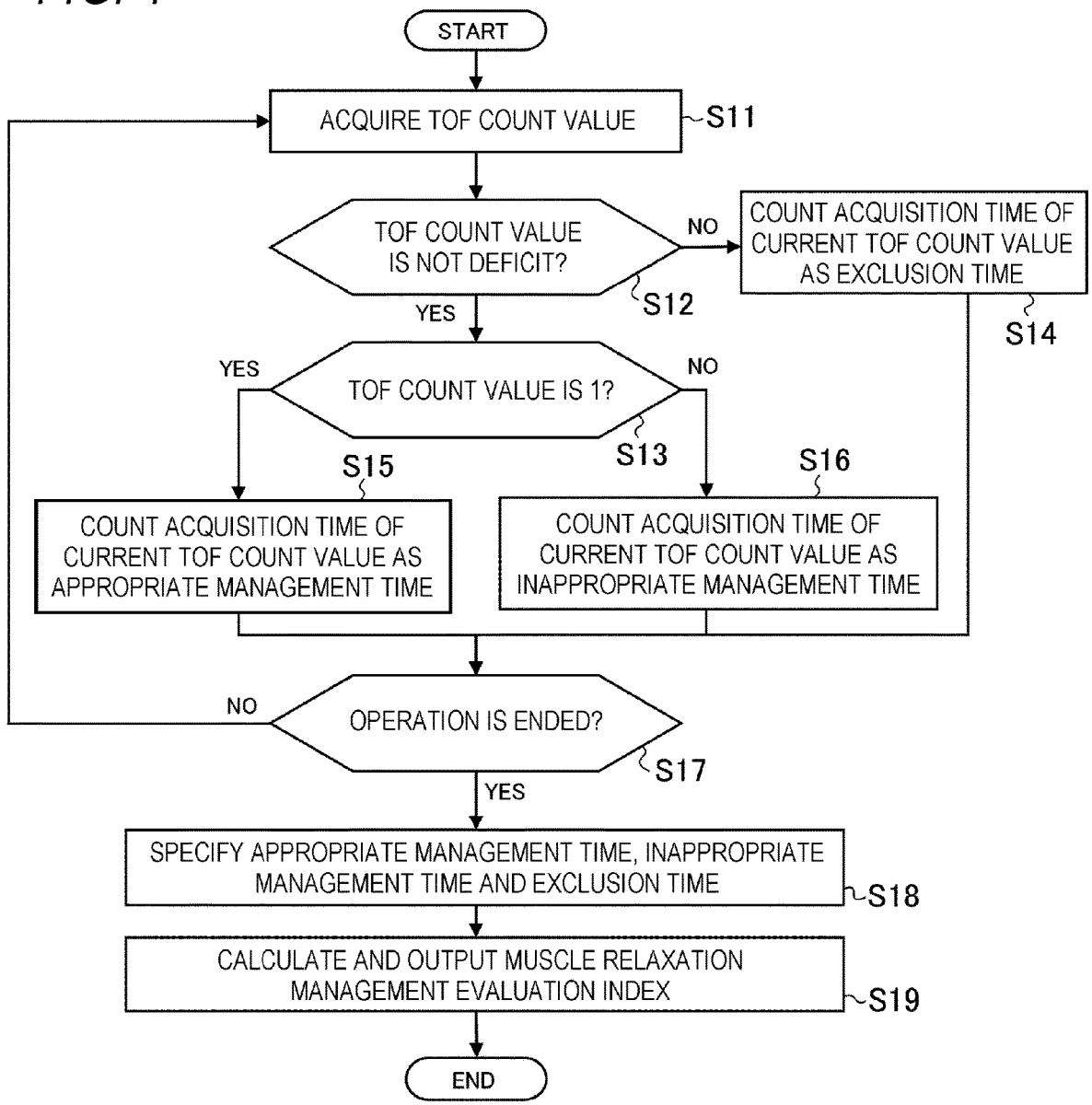
FIG. 4 is a flowchart illustrating a method of calculating a muscle relaxation management evaluation index.

Next, the method of calculating the muscle relaxation management evaluation index, which is the evaluation index for the muscle relaxation management of the patient P to which the muscle relaxant is administered, will be described below with reference to FIG. 4. FIG. 4 is a flowchart illustrating the method of calculating the muscle relaxation management evaluation index.

As illustrated in FIG. 4, when the operation of the patient P to which the muscle relaxant is administered is started in step S11, the control unit 2 acquires the stimulus-response data (TOF count value in this example) indicating the stimulus-response of the patient P from the stimulus-response sensor 12. Next, the control unit 2 determines whether the TOF count value is a deficit value (step S12). When the TOE count value is not a deficit value (YES in step S12), the control unit 2 determines whether the acquired TOF count value is 1 (step S13). When the TOF count value is a deficit value (NO in step S12), the control unit 2 counts an acquisition time of the current TOF count value as the exclusion time (step S14).

Next, in step S13, when the TOF count value is 1 (YES in step S13), the control unit 2 determines that the muscle relaxation management of the patient P is appropriate, and then counts the acquisition time of the current TOF count value as the appropriate management time (step S15). The term "appropriate management time" as used herein refers to a time when the muscle relaxation management is appropriately performed on the patient P. On the other hand, when the TOF count value is not 1 (in other words, when the TOF count value is 0, 2, 3, or 4) (NO in step S13), the control unit 2 determines that the muscle relaxation management of the patient P is not appropriate, and counts the acquisition time of the current TOF count value as the inappropriate management time (step S16). The term "inappropriate management time" as used herein refers to a time when the muscle relaxation management is not appropriately performed on the patient P.

Next, when the operation of the patient P is not ended (NO in step S17), the processes of steps S11 to S16 are repeatedly performed. For example, when the TOF stimulation is applied to the patient P at intervals of 15 seconds, the processes of steps S11 to S16 may be repeatedly performed every 15 seconds. In this case, the acquisition time of the current TOF count value (15 seconds), which is a time from timing when a previous TOF count value is acquired to timing when the current TOF count value is acquired, is counted as the appropriate management time or the inappropriate management time. On the other hand, when the operation of the patient P is ended (YES in step S17), the process proceeds to step S18.

Next, the control unit 2 specifies the appropriate management time, the inappropriate management time, and the exclusion time counted during the operation time (step S18). Thereafter, the control unit 2 calculates a muscle relaxation management evaluation index Pm based on the operation time, the appropriate management time, and the exclusion time (step S19). For example, the muscle relaxation management evaluation index Pm may be calculated based on the following formula (2).

$$Pm=Tr3/(T0-Te3)\times 100\% \qquad (2)$$

Here, Tr3 refers to the appropriate management time, T0 refers to the operation time, and Te3 refers to the exclusion time. For example, when the operation time T0 is 300 minutes, the exclusion time Te3 is 4 minutes, and the appropriate management time Tr3 is 260 minutes, the muscle relaxation management evaluation index Pm is about 88%.

Thereafter, the control unit 2 outputs the calculated muscle relaxation management evaluation index Pm (step S19). For example, the control unit 2 may display information on the muscle relaxation management evaluation index Pm on the display unit 5. In particular, the control unit 2 may display the information on the muscle relaxation management evaluation index Pm on a display screen on which information on the TOF count value and/or the TOF ratio is displayed. Further, the control unit 2 may store the information on the muscle relaxation management evaluation index Pm in the storage device 3 in a state of being associated with the information on the operation of the patient P.

According to the present embodiment, after the appropriate management time, the inappropriate management time, and the exclusion time are specified based on the TOF count value, the muscle relaxation management evaluation index Pm is calculated based on the operation time T0, the appropriate management time Tr3, and the exclusion time Te3, and then the muscle relaxation management evaluation index Pm is output. In this way, it is possible to objectively digitalize and visualize skillfulness of the muscle relaxation management based on the muscle relaxation management evaluation index Pm. By presenting the information on the muscle relaxation management evaluation index Pm to the anesthetist who is in charge of the operation of the patient P, the anesthetist can know an objective evaluation of the muscle relaxation management. Further, when the anesthesia management, of the patient P is performed by the automatic anesthesia management system, it is possible to objectively evaluate the skillfulness of the muscle relaxation management performed by the automatic anesthesia management system through the muscle relaxation management evaluation index Pm.

Although the muscle relaxation management evaluation index Pm is output when the operation of the patient is ended in the present embodiment, the muscle relaxation management evaluation index Pm may also be output during the operation of the patient P. In this case, the muscle relaxation management evaluation index Pm may be sequentially updated along with the progress of the operation. When the muscle relaxation management evaluation index Pm is output during the operation of the patient P, the operation time TO is the time from the operation start time is to the current time tc. At this time, the determination of whether the operation is ended in step S17 performed by the control unit 2 may be performed after step S19.

Although the TOF count value is adopted as an example of the stimulus-response data indicating the stimulus-response of the patient P in the present embodiment, a parameter other than the TOF count value may be adopted as the stimulus-response data. For example, the TOF ratio (T4/T1) may be adopted as the stimulus-response data. In this case, in the determination process of step S13, the control unit 2 determines whether the TOF ratio satisfies a condition of 1%≤TOF ratio≤10%. When the condition that the TOF ratio is 1% to 10% is satisfied (YES in step S13), the control unit 2 may count an acquisition time of a current TOF ratio as the appropriate management time (step S15). On the other hand, when the condition that the TOE ratio is 1% to 10% is not satisfied (NO in step S13), the control unit 2 may count the acquisition time of the current TOF ratio as the inappropriate management time (step S16).

In a case where the muscle relaxant is rapidly administered to the patient P, even when the TOF count value is 0 during a certain period of time from the start of the operation, the certain period of time may be determined as the appropriate management time.

(Analgesic Management Evaluation Index)

Figure 5:
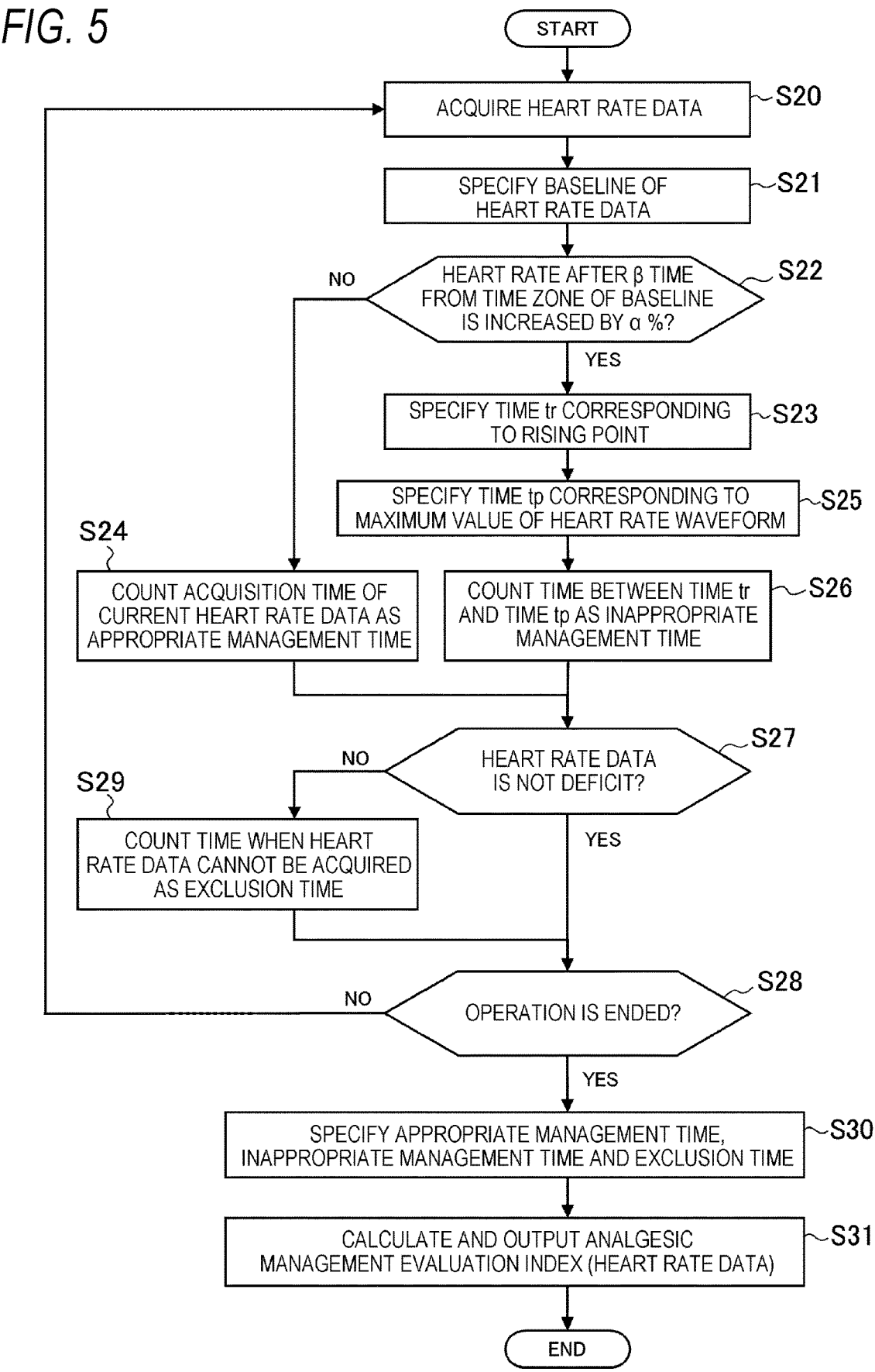
FIG. 5 is a flowchart illustrating a method of calculating an analgesic management evaluation index.
Figure 6:
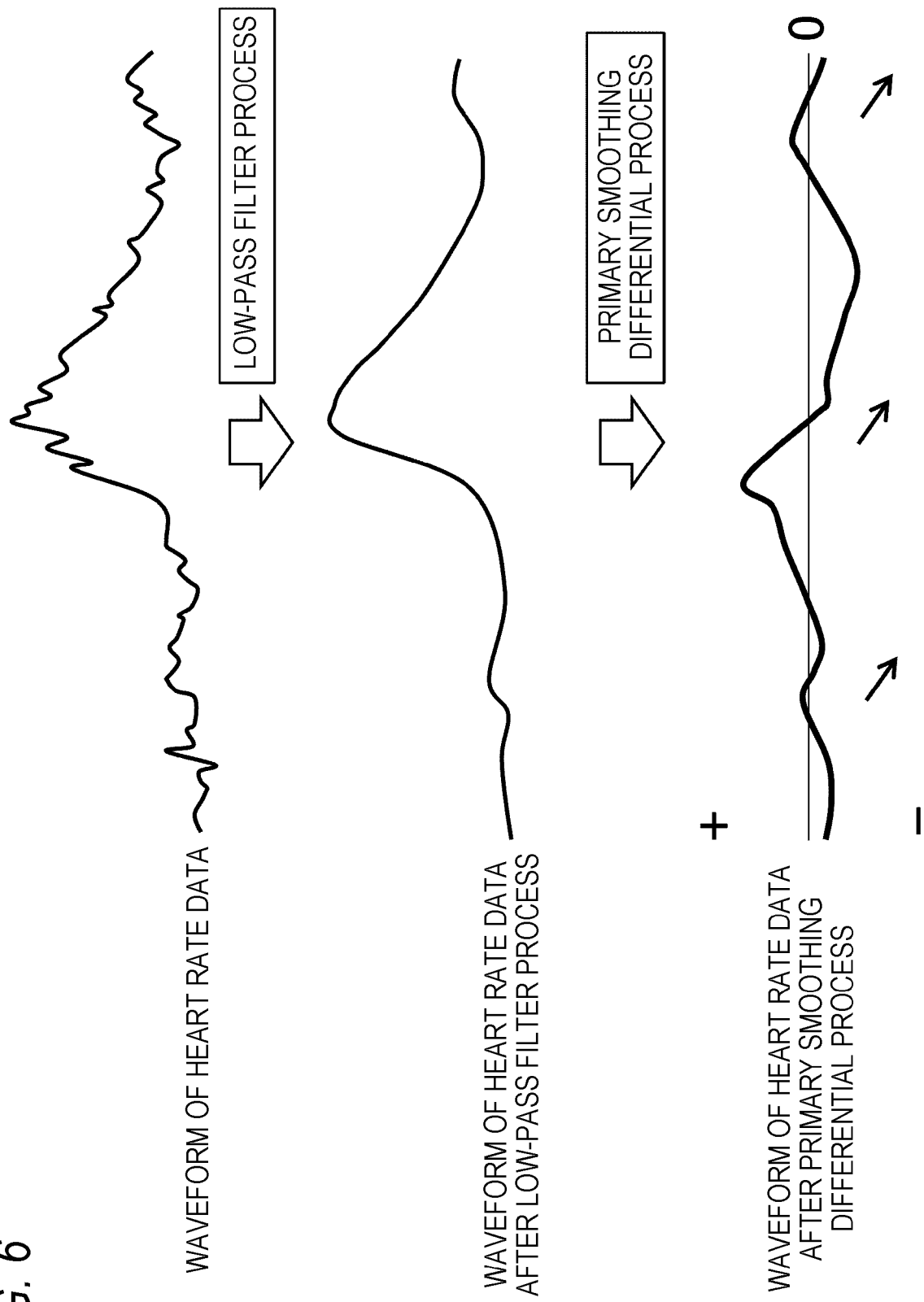
FIG. 6 illustrates a procedure for calculating a maximum value of a waveform of heart rate data.
Figure 7:
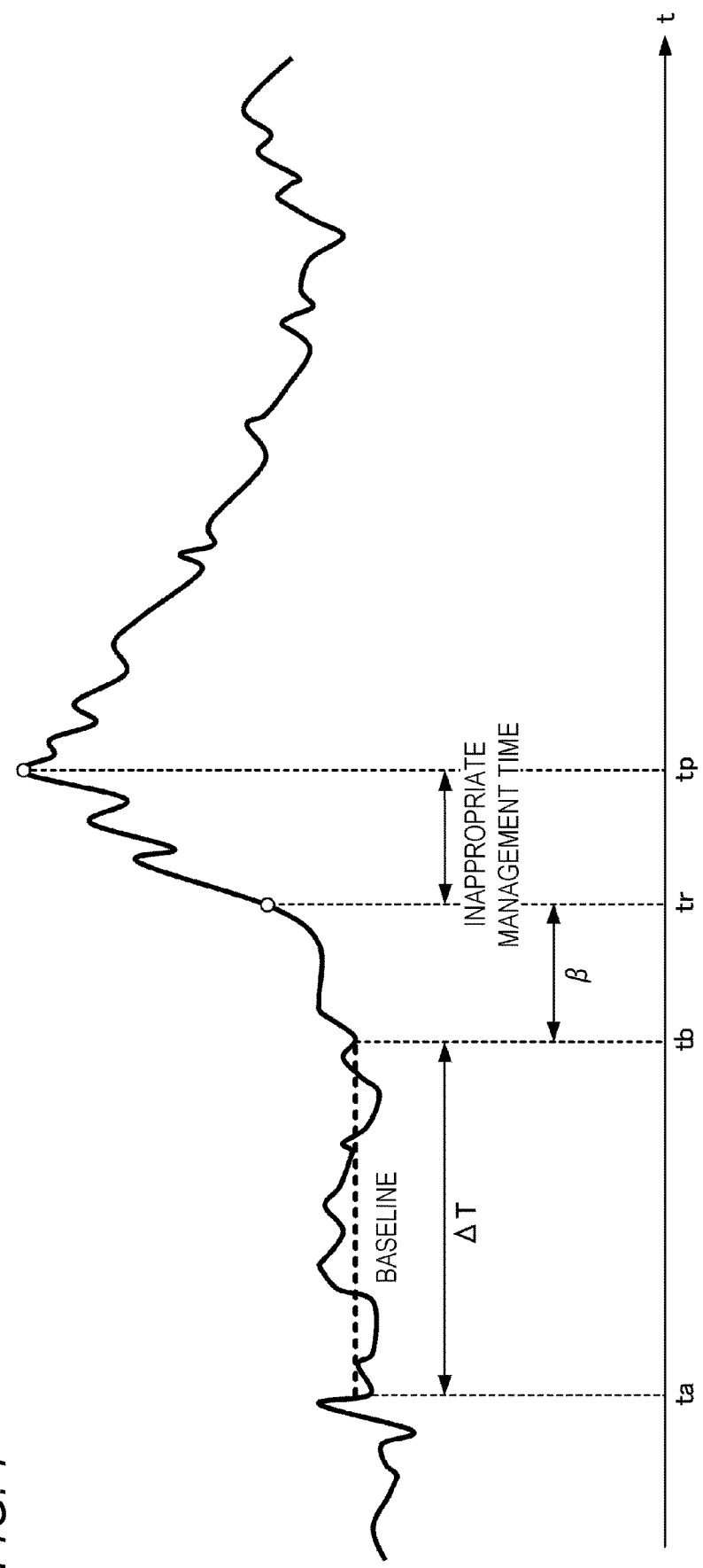
FIG. 7 illustrates a process of specifying an inappropriate management time based on the heart rate data.

Next, the analgesic management evaluation index, which is the evaluation index for the analgesic management of the patient P to which the analgesic is administered, will be described below with reference to FIGS. 5 to 7. FIG. 5 is a flowchart illustrating the method of calculating the analgesic management evaluation index. FIG. 6 illustrates a procedure for calculating a maximum value of a waveform of heart rate data. FIG. 7 illustrates a process of specifying the inappropriate management time based on the heart rate data.

As illustrated in FIG. 5, when the operation of the patient P to which the analgesic is administered is started in step S20, the control unit 2 acquires the pulse wave data indicating the change over time in the pulse wave of the patient P or the electrocardiogram data indicating the change over time in the electrocardiogram of the patient P from the pain reaction sensor 13. In a case where the control unit 2 acquires the electrocardiogram data, the pain reaction sensor 13 may be an electrocardiogram sensor. On the other hand, in a case where the control unit 2 acquires the pulse wave data, the pain reaction sensor 13 may be a pulse wave sensor. Next, the control unit 2 acquires the heart rate data (an example of the pain reaction data) indicating a change over time in heart rate of the patient P based on the received pulse wave data or electrocardiogram data.

Next, in step S21, the control unit 2 specifies a baseline of the heart rate data of the patient P as illustrated in FIG. 7. The baseline indicates an average value of the heart rate data continuously acquired from the patient P in a time zone $\Delta T$ (for example, in four minutes). A body movement noise or the like in the heart rate data may be specified as a deficit value. Thereafter, the baseline may be calculated by excluding the deficit value from the time zone $\Delta T$. In the example illustrated in FIG. 7, the time zone $\Delta T$ of the baseline is a time zone between a start time to and an end time tb.

Next, in step S22, the control unit 2 determines whether the heart rate after $\beta$ seconds (for example, 60 seconds) from the end time tb of the time zone $\Delta T$ of the baseline is increased by $\alpha\%$ from the baseline. When the control unit 2 determines that the heart rate is increased by $\alpha\%$ from the baseline (YES in step S22), the control unit 2 specifies a time tr ($\alpha\%$ time corresponding to a rising point) corresponding to the heart rate increased by $\alpha\%$ from the baseline. For example, when $\alpha$ is 20% while a value of the baseline is Nav, heart rate Nr at the time tr satisfies Nr=1.2 Nav. It should be noted that a is not limited to 20%.

On the other hand, when it is determined that the heart rate is not increased by $\alpha\%$ from the baseline (NO in step S22), the control unit 2 determines that the analgesic management of the patient P is appropriate, and then counts an acquisition time of current heart rate data as the "appropriate management time" (step S24).

Next, in step S25, the control unit 2 specifies a time tp corresponding to a maximum value of a heart rate waveform including a high frequency component which appears after the time tr corresponding to the rising point and is acquired during the operation of the patient P. In the present embodiment, first, the control unit 2 removes the high frequency component (for example, a frequency component of 0.003 Hz) from the heart rate waveform by performing a low-pass filter process on the heart rate waveform. Next, the control unit 2 performs a primary smoothing differential process on the heart rate waveform from which the high frequency component is removed, thereby specifying the maximum value in the heart rate waveform.

Next, in step S26, the control unit 2 counts a time between the time tr corresponding to the rising point and the time tp corresponding to the maximum value of the heart rate waveform including the high frequency component as the inappropriate management time. The term "inappropriate management time" as used herein refers to a time when the analgesic management is not appropriately performed on the patient P.

Next, the control unit 2 determines whether there is no deficit value in the heart rate data (step S27). When there is a deficit value in the heart rate data (NO in step S27), the control unit 2 counts a time when the deficit value is acquired as the exclusion time (step S29).

Next, the control unit 2 determines whether the operation of the patient P is ended (step S28). When the operation of the patient P is not ended (NO in step S28), the processes of steps S20 to S29 are repeatedly performed. On the other hand, when the operation of the patient P is ended (YES in step S28), the process proceeds to step S30.

Next, in step S30, the control unit 2 specifies an appropriate management time Tr2, which is a time when the analgesic management is appropriately performed, based on the operation time T0, an inappropriate management time Tn2, and an exclusion time Te2. Specifically, the control unit 2 may calculate the appropriate management time Tr2 based on the following formula (3).

$$Tr2 = T0 - Tn2 - Te2 \tag{3}$$

Next, the control unit 2 calculates an analgesic management evaluation index Pa based on the operation time T0, the appropriate management time Tr2, and the exclusion time Te2 (step S31). For example, the analgesic management evaluation index Pa may be calculated based on the following formula (4).

$$Pa = Tr2/(T0 - Te2) \times 100\% \tag{4}$$

Thereafter, the control unit 2 outputs the calculated analgesic management evaluation index Pa (step S31). For example, the control unit 2 may display information on the analgesic management evaluation index Pa on the display unit 5. In particular, the control unit 2 may display the information on the analgesic management evaluation index Pa on a display screen on which information on the heart rate data is displayed. Further, the control unit 2 may store the information on the analgesic management evaluation index Pa in the storage device 3 in a state of being associated with the information on the operation of the patient P.

According to the present embodiment, after the inappropriate management time Tn2 and the exclusion time Te2 are specified based on the heart rate data, the appropriate management time Tr2 is specified based on the inappropriate management time Tn2 and the exclusion time Te2. Thereafter, the analgesic management evaluation index Pa is calculated based on the operation time TO, the appropriate management time Tr2, and the exclusion time Te2, and then the analgesic management evaluation index Pa is output. In this way, it is possible to objectively digitalize and visualize skillfulness of the analgesic management based on the analgesic management evaluation index Pa. By presenting the information on the analgesic management evaluation index Pa to the anesthetist who is in charge of the operation of the patient P, the anesthetist can know an objective evaluation of the analgesic management. Further, when the anesthesia management of the patient P is performed by the automatic anesthesia management system, it is possible to objectively evaluate the skillfulness of the analgesic management performed by the automatic anesthesia management system through the analgesic management evaluation index Pa.

Although the analgesic management evaluation index Pa is output when the operation of the patient P is ended in the present embodiment, the analgesic management evaluation index Pa may also be output during the operation of the patient P. In this case, the analgesic management evaluation index Pa may be sequentially updated along with the progress of the operation. When the analgesic management evaluation index Pa is output during the operation of the patient P, the operation time T0 is a time from the operation start time ts to the current time tc. At this time, the determination in step S28 of the control unit 2 may be performed after step S31.

Although the heart rate data is adopted as an example of the pain reaction data indicating the pain reaction of the patient P in the present embodiment, physiological information data other than the heart rate data may be adopted as the pain reaction data. For example, the blood pressure data indicating the change over time in the blood pressure (systolic blood pressure or diastolic blood pressure) of the patient P may be adopted as the pain reaction data. In this case, the control unit 2 acquires the blood pressure data of the patient P from the blood pressure sensor, and then performs the processes of steps S21 to S28. That is, in step S21, the control unit 2 determines whether there is a maximum value in a waveform of the blood pressure data (hereinafter, referred to as a blood pressure waveform), and then performs each process of steps S22 to S28 when there is a maximum value in the blood pressure waveform.

(Another Example of Method of Calculating Analgesic Management Evaluation Index)

Figure 8:
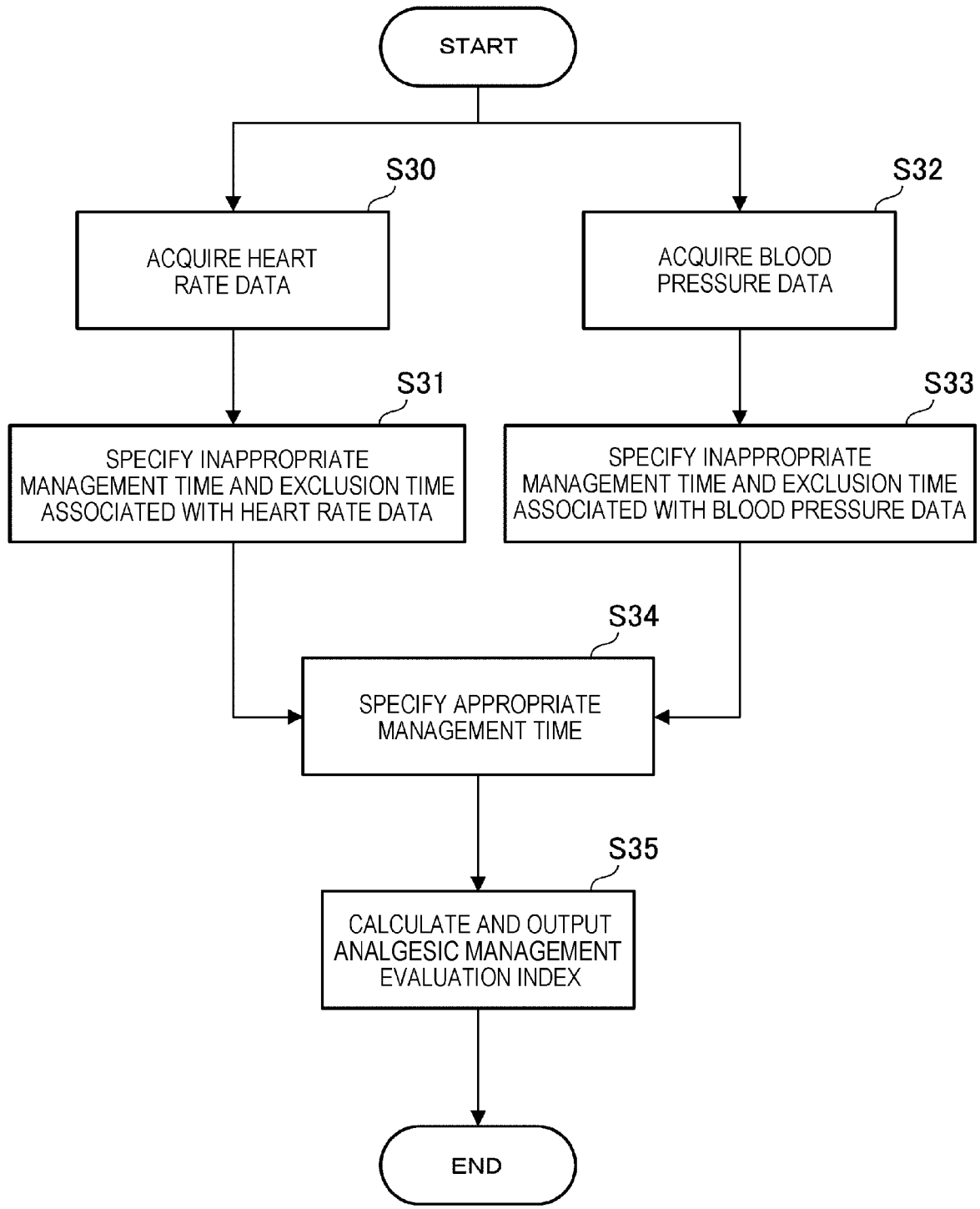
FIG. 8 is a flowchart illustrating a method of using two types of pain reaction data including the heart rate data and blood pressure data to calculate the analgesic management evaluation index.

Next, another example of the method of calculating the analgesic management evaluation index Pa will be described below with reference to FIGS. 8 to 10. FIG. 8 is a flowchart illustrating a method of using two types of the pain reaction data including the heart rate data and the blood pressure data to calculate the analgesic management evaluation index Pa. In the present example, after the inappropriate management time and the exclusion time of the analgesic management are respectively calculated for each of the heart rate data and the blood pressure data, the appropriate management time of the analgesic management is specified based on the two calculated inappropriate management times and the two calculated exclusion times. In the present example, the pain reaction sensor 13 can include a blood pressure sensor and a pulse wave sensor.

As illustrated in FIG. 8, in step S30, the control unit 2 acquires the pulse wave data from the pulse wave sensor, and then acquires the heart rate data of the patient P based on the pulse wave data. Next, the control unit 2 specifies an inappropriate management time Tn21 and an exclusion time Te21 associated with the heart rate data (step S31). In particular, the control unit 2 can specify the inappropriate management time Tn21 and the exclusion time Te21 associated with the heart rate data through the processes of steps S21 to S26 illustrated in FIG. 5.

Next, in step S32, the control unit 2 acquires the blood pressure data from the blood pressure sensor. Thereafter, the control unit 2 specifies an inappropriate management time Tn22 and an exclusion time Te22 associated with the blood pressure data (step S33). In particular, the control unit 2 can specify the inappropriate management time Tn22 and the exclusion time Te22 associated with the blood pressure data through the processes of steps S21 to S26 illustrated in FIG. 5 (here, it is assumed that the pain reaction data subjected to the processes illustrated in FIG. 5 is replaced from the heart rate data to the blood pressure data).

In step S34, the control unit 2 specifies the appropriate management time Tr2 of the analgesic management based on the inappropriate management time Tn21 and the exclusion time Te21 associated with the heart rate data and the inappropriate management time Tn22 and the exclusion time Te22 associated with the blood pressure data.

Thereafter, the control unit 2 calculates the analgesic management evaluation index Pa based on the operation time T0, the appropriate management time Tr2, the exclusion time Te21, and the exclusion time Te22 (step S35). For example, the analgesic management evaluation index Pa may be calculated based on the following formula (5).

$$Pa = Tr2/(T0 - Te21 - Te22) \times 100\% \quad (5)$$

Concerning this point, as illustrated in FIG. 9, the control unit 2 may calculate the analgesic management evaluation index Pa through an AND operation process of the inappropriate management time Tn21 associated with the heart rate data and the inappropriate management time Tn22 associated with the blood pressure data. As illustrated in FIG. 10, the control unit 2 may also calculate the analgesic management evaluation index Pa through an OR operation process of the inappropriate management time Tn21 associated with the heart rate data and the inappropriate management time Tn22 associated with the blood pressure data.

(AND Operation Process of Inappropriate Management Time Tn21 and Inappropriate Management Time Tn22)

The control unit 2 can calculate the analgesic management evaluation index Pa based on the AND operation process of the inappropriate management time Tn21 and the inappropriate management time Tn22. For example, as illustrated in FIG. 9, it is assumed that the inappropriate management time Tn21 associated with the heart rate data is defined by a time between a time t1 corresponding to a rising point of the heart rate waveform and a time t2 corresponding to the maximum value of the heart rate waveform. It is also assumed that the inappropriate management time Tn22 associated with the blood pressure data is defined by a time between a time t3 corresponding to a rising point of the blood pressure waveform and a time t4 corresponding to the maximum value of the blood pressure waveform.

Figure 9A:
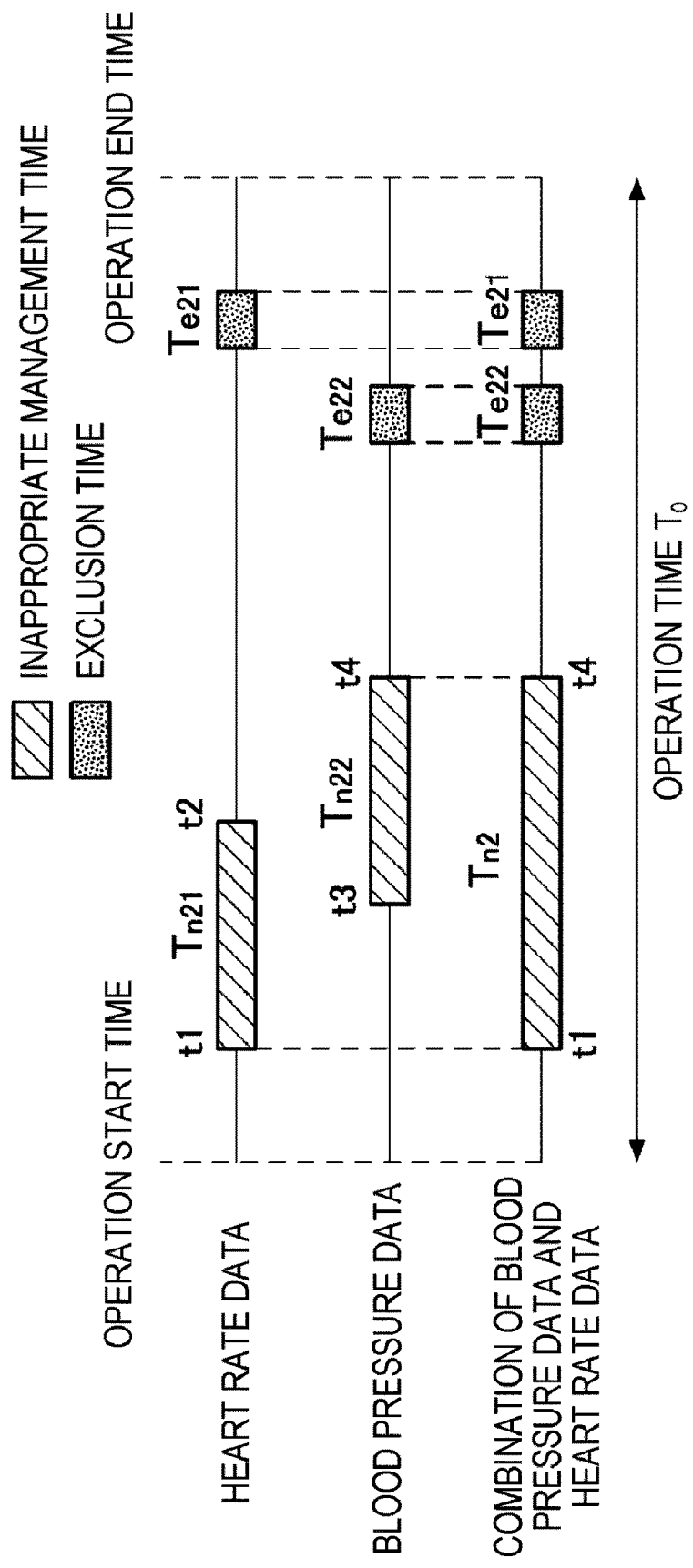
FIG. 9A illustrates a method of calculating the analgesic management evaluation index through an AND operation process of an inappropriate management time associated with the heart rate data and an inappropriate management time associated with the blood pressure data (part 1).

In the state illustrated in FIG. 9A, since the inappropriate management time Tn21 and the inappropriate management time Tn22 at least partially overlap each other, the control unit 2 determines that a time between the time t1 corresponding to the rising point of the heart rate waveform and the time t4 corresponding to the maximum value of the blood pressure waveform is the inappropriate management time Tn2 of the analgesic management.

Thereafter, the control unit 2 specifies the appropriate management time Tr2 of the analgesic management based on the operation time T0, the inappropriate management time Tn2, and the exclusion times Te21 and Te22. In particular, the control unit 2 may calculate the appropriate management time Tr2 based on the following formula (6). Thereafter, the control unit 2 can calculate the analgesic management evaluation index Pa based on the above formula (5).

$$Tr2 = T0 - Tn2 - Te21 - Te22 \quad (6)$$

Figure 9B:
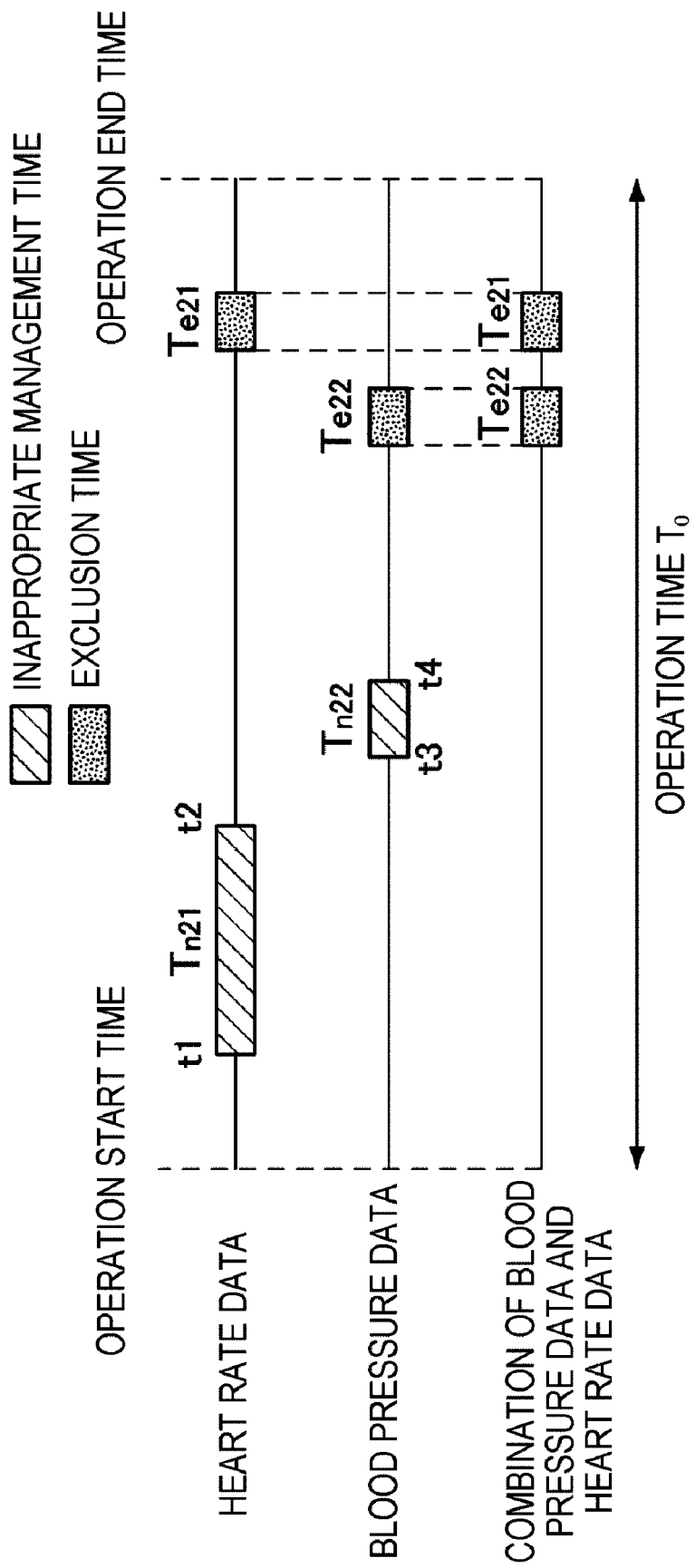
FIG. 9B illustrates the method of calculating the analgesic management evaluation index through the AND operation process of the inappropriate management time associated with the heart rate data and the inappropriate management time associated with the blood pressure data (part 2).

Meanwhile, in the state illustrated in FIG. 9B, since the inappropriate management time Tn21 and the inappropriate management time Tn22 do not overlap each other at all, the control unit 2 determines that the inappropriate management time Tn2 of the analgesic management is zero. When a time difference between the time t3 and the time t2 is sufficiently small, the control unit 2 may determine that a sum of the inappropriate management time Tn21 and the inappropriate management time Tn22 is the inappropriate management time Tn2 of the analgesic management (Tn2=Tn21+Tn22).

(OR Operation Process of Inappropriate Management Time Tn21 and Inappropriate Management Time Tn22)

The control unit 2 can calculate the analgesic management evaluation index Pa based on the OR operation process of the inappropriate management time Tn21 and the inappropriate management time Tn22. For example, as illustrated in FIG. 10, it is assumed that the inappropriate management time Tn21 associated with the heart rate data is defined by the time between the time t1 corresponding to the rising point of the heart rate waveform and the time t2 corresponding to the maximum value of the heart rate waveform. It is also assumed that the inappropriate management time Tn22 associated with the blood pressure data is defined by the time between the time t3 corresponding to the rising point of the blood pressure waveform and the time t4 corresponding to the maximum value of the blood pressure waveform.

Figure 10:
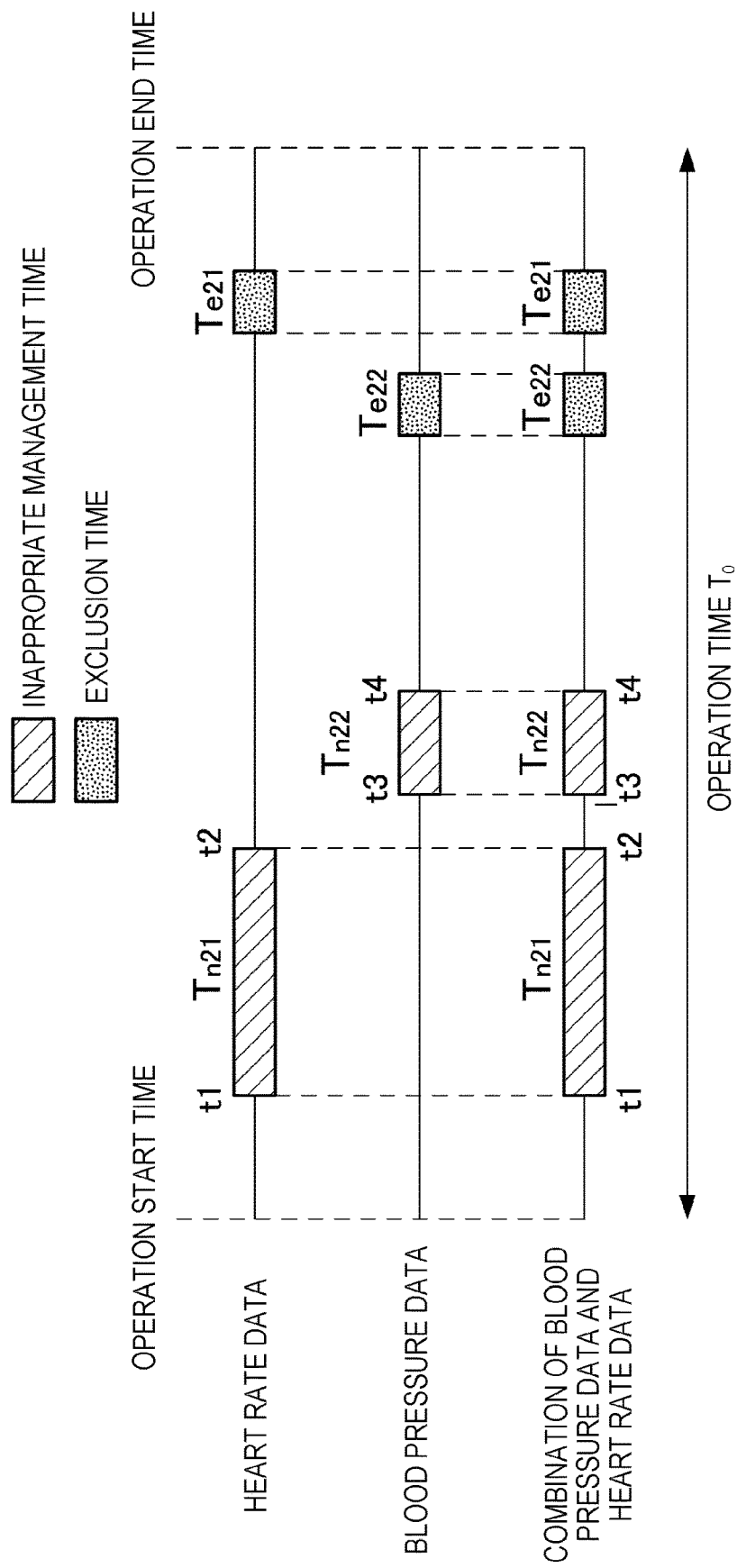
FIG. 10 illustrates a method of calculating the analgesic management evaluation index through an OR operation process of the inappropriate management time associated with the heart rate data and the inappropriate management time associated with the blood pressure data.

In the state illustrated in FIG. 10, the inappropriate management time Tn21 and the inappropriate management time Tn22 do not overlap each other at all, and the control unit 2 determines that the sum of the inappropriate management time Tn21 and the inappropriate management time Tn22 is the inappropriate management time Tn2 of the analgesic management (Tn2=Tn21+Tn22). Thereafter, the control unit 2 calculates the appropriate management time Tr2 based on the operation time T0, the inappropriate management time Tn2, the exclusion times Te21 and Te22, and the above formula (6). Thereafter, the control unit 2 can calculate the analgesic management evaluation index Pa based on the above formula (5).

According to the present example, the analgesic management evaluation index Pa of the analgesic management is calculated based on the various parameters related to the heart rate data and the various parameters related to the blood pressure data. In this way, since the analgesic management evaluation index Pa is calculated through using the two types of pain reaction data including the heart rate data and the blood pressure data, the analgesic management evaluation index Pa can be calculated in accordance with actual analgesic management.

(Comprehensive Anesthesia Management Evaluation Index)

Next, a comprehensive anesthesia management evaluation index which is a comprehensive evaluation index for the anesthesia management of the patient P to which the anesthetics (sedative, analgesic, and muscle relaxant) are administered, will be described below with reference to FIGS. 11 and 12.

Here, the anesthesia management of the patient P refers to comprehensive anesthesia management including the sedative management, the analgesic management, and the muscle relaxation management. FIG. 11 is a flowchart illustrating an example of a method of calculating the comprehensive anesthesia management evaluation index Pk. FIG. 12 illustrates a method of calculating the comprehensive anesthesia management evaluation index Pk based on various parameters related to the sedative management, various parameters related to the analgesic management, and various parameters related to the muscle relaxation management.

Figure 12:
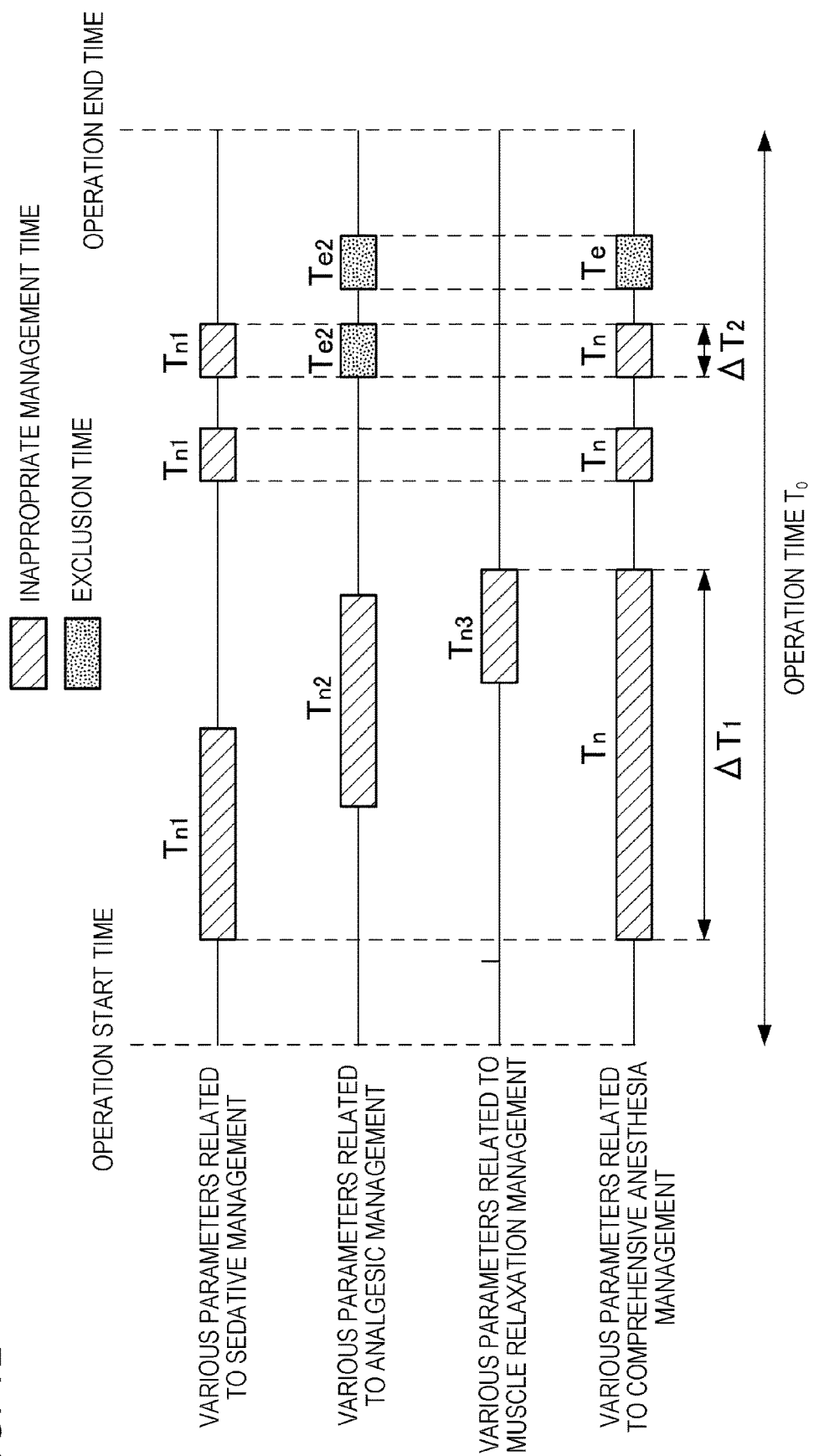
FIG. 12 illustrates a method of calculating the comprehensive anesthesia management evaluation index based on various parameters related to sedative management, various parameters related to analgesic management, and various parameters related to muscle relaxation management.

In FIG. 12, the inappropriate management time and the exclusion time are illustrated, while the appropriate management time is not illustrated. Concerning this point, it is assumed that a time other than the inappropriate management time and the exclusion time among the operation time is the appropriate management time.

Figure 11:
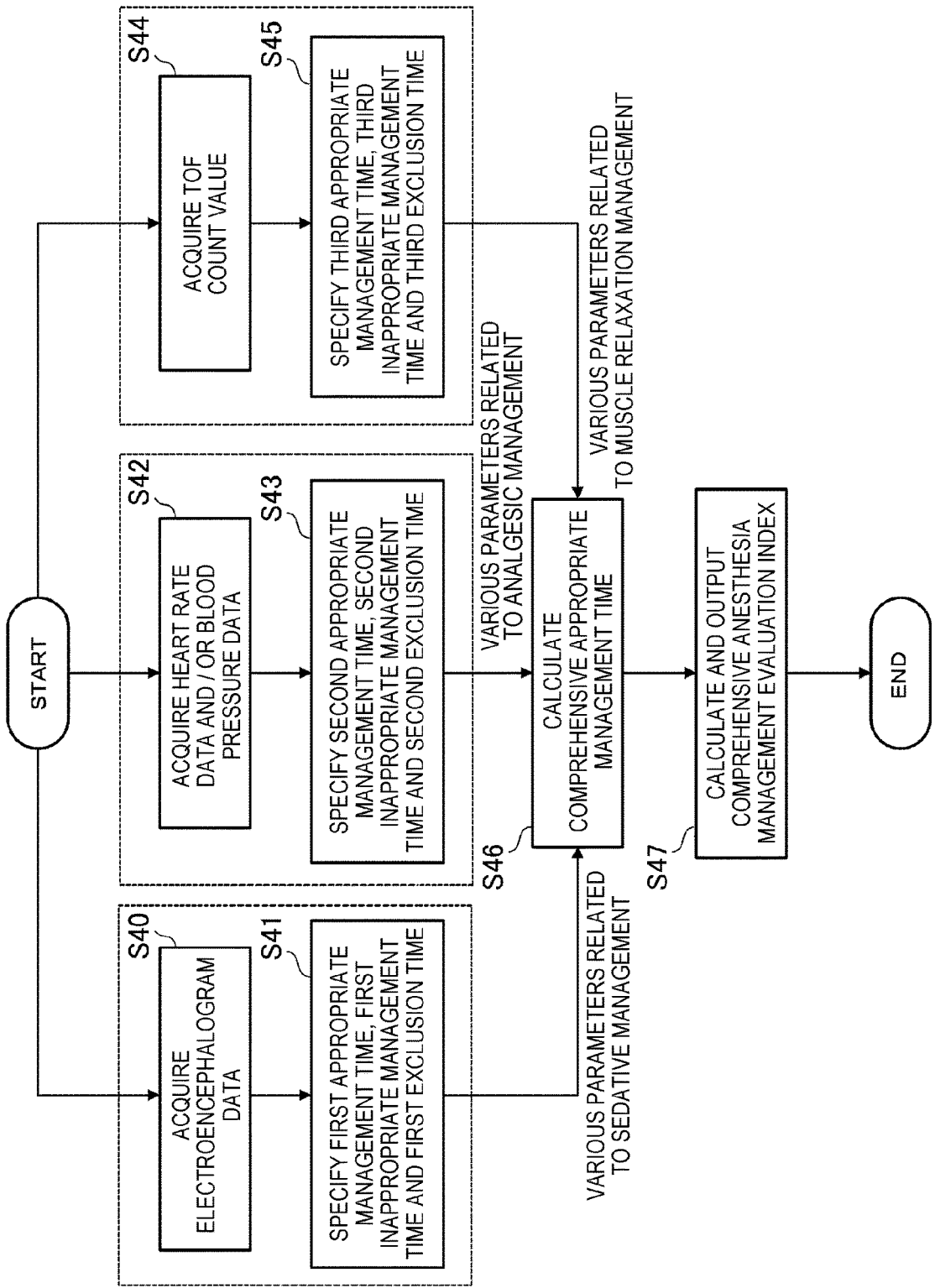
FIG. 11 is a flowchart illustrating an example of a method of calculating a comprehensive anesthesia management evaluation index.

As illustrated in FIG. 11, in step S40, the control unit 2 acquires the electroencephalogram data from the electroencephalogram sensor 10. Thereafter, the control unit 2 specifies the first appropriate management time Tr1, the first inappropriate management time Tn1, and the first exclusion time Te1 related to the sedative management (electroencephalogram data) (step S41). Concerning this point, the control unit 2 can specify the first appropriate management time Tr1, the first inappropriate management time Tn1, and the first exclusion time Te1 through the processes of steps S2 to S9 illustrated in FIG. 3.

Next, in step S42, the control unit 2 acquires the heart rate data and or the blood pressure data as the pain reaction data. In particular, the control unit 2 may acquire the heart rate data based on the electrocardiogram data or the pulse wave data transmitted from the pain reaction sensor 13. Further, the control unit 2 may acquire the blood pressure data from the pain reaction sensor 13. Next, the control unit 2 specifies the second appropriate management time Tr2, the second inappropriate management time Tn2, and the second exclusion time Te2 related to the analgesic management (pain reaction data) (step S43). Concerning this point, the control unit 2 can specify the second appropriate management time Tr2, the second inappropriate management time Tn2, and the second exclusion time Te2 through the processes of steps S21 to S27 illustrated in FIG. 5.

Next, in step S44, the control unit 2 acquires the TOF count value from the stimulus-response sensor 12. Thereafter, the control unit 2 specifies the third appropriate management time Tr3, the third inappropriate management time Tn3, and the third exclusion time Te3 related to the muscle relaxation management (TOF count value) (step S45). Concerning this point, the control unit 2 can specify the third appropriate management time Tr3, the third inappropriate management time Tn3, and the third exclusion time Te3 through the processes of steps S12 to S16 illustrated in FIG. 4.

Thereafter, the control unit 2 calculates the comprehensive appropriate management time Tr based on the various parameters related to the sedative management (the first inappropriate management time Tn1 and the like), the various parameters related to the analgesic management (the second inappropriate management time Tn2 and the like), and the various parameters related to the muscle relaxation management (the third inappropriate management time Tn3 and the like) (step S46). Concerning this point, a method of calculating a comprehensive appropriate management time Tr will be described below with reference to FIG. 12.

As illustrated in FIG. 12, in the present example, it is assumed that there is no exclusion time Te1 related to the analgesic management and no exclusion time Te3 related to the muscle relaxation management. When calculating the comprehensive appropriate management time Tr, priorities of the various parameters are as follows.

Inappropriate Management Time>Exclusion Time>Appropriate Management Time

Therefore, in a case where the inappropriate management time, the exclusion time, and the appropriate management time overlap each other in a predetermined time zone, the predetermined time zone is determined as the inappropriate management time. Further, in a case where the exclusion time and the appropriate management time overlap each other in the predetermined time zone, the predetermined time zone is determined as the exclusion time. For example, as illustrated in FIG. 12, when the first inappropriate management time Tn1 related to the sedative management and the second exclusion time Te2 related to the analgesic management overlap each other in a time zone ΔT2, the time zone ΔT2 is determined as a comprehensive inappropriate management time Tn.

Further, as illustrated in the drawing, when the first inappropriate management time Tn1, the second inappropriate management time Tn2, and the third inappropriate management time Tn3 exist in a time zone ΔT1, the control unit 2 determines that the time zone ΔT1 is the comprehensive inappropriate management time Tn.

As described above, the control unit 2 specifies the comprehensive inappropriate management time Tn and a comprehensive exclusion time Te based on the various parameters related to the sedative management, the various parameters related to the analgesic management, and the various parameters related to the muscle relaxation management. Thereafter, the control unit 2 calculates the comprehensive appropriate management time Tr based on the following formula (7).

$$Tr=T0-Tn-Te \quad (7)$$

Next, the control unit 2 calculates the comprehensive anesthesia management evaluation index Pk based on the operation time T0, the comprehensive appropriate management time Tr, the comprehensive exclusion time Te, and the following formula (8) (step S47).

$$Pk=Tr/(T0-Te)\times100\% \quad (8)$$

Thereafter, the control unit 2 outputs the calculated comprehensive anesthesia management evaluation index Pk. For example, the control unit 2 may display information on the comprehensive anesthesia management evaluation index Pk on the display unit 5. In particular, the control unit 2 may display the information on the comprehensive anesthesia management evaluation index Pk on a display screen on which information on the anesthesia management (the sedative management, the analgesic management, and the muscle relaxation management) is displayed. The control unit 2 may store the information on the comprehensive anesthesia management evaluation index Pk in the storage device 3 in a state of being associated with the information on the operation of the patient P. Further, information on the comprehensive anesthesia management evaluation index Pk, the sedative management evaluation index Ps, the muscle relaxation management evaluation index Pm, and the analgesic management evaluation index Pa may be stored in the storage device 3 together with the information on the operation of the patient P.

According to the present embodiment, the comprehensive anesthesia management evaluation index Pk, which is a comprehensive evaluation index for the anesthesia management of the patient P, is calculated based on the various parameters related to the sedative management, the various parameters related to the analgesic management, and the various parameters related to the muscle relaxation management. In this way, skillfulness of the sedative management, the analgesic management, and the muscle relaxation management can be comprehensively and objectively digitalized and visualized through the comprehensive anesthesia management evaluation index Pk. By presenting the information on the comprehensive anesthesia management evaluation index Pk to the anesthetist who is in charge of the operation of the patient P, the anesthetist can know a comprehensive and objective evaluation of the anesthesia management. Further, when the anesthesia management of the patient P is performed by the automatic anesthesia management system, it is possible to comprehensively and objectively evaluate the skillfulness of the anesthesia management performed by the automatic anesthesia management system through the comprehensive anesthesia management evaluation index Pk.

(Modification of Method of Calculating Comprehensive Anesthesia Management Evaluation Index)

Figure 13:
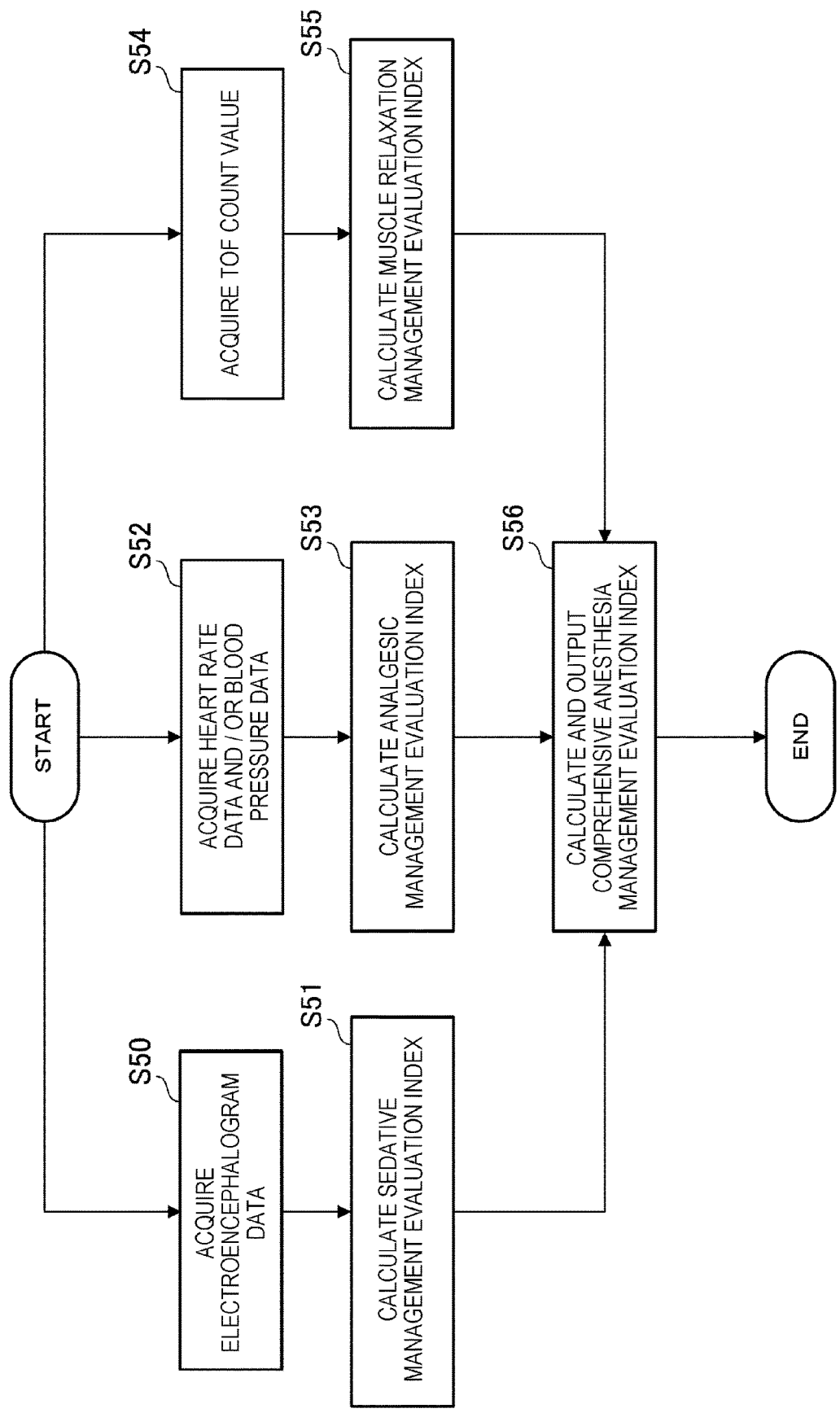
FIG. 13 is a flowchart illustrating a modification of the method of calculating the comprehensive anesthesia management evaluation index.

Next, a modification of the method of calculating the comprehensive anesthesia management evaluation index Pk will be described below with reference to FIG. 13. FIG. 13 is a flowchart illustrating the modification of the method of calculating the comprehensive anesthesia management evaluation index Pk.

As illustrated in FIG. 13, in step S50, the control unit 2 acquires the electroencephalogram data from the electroencephalogram sensor 10, and then calculates the sedative management evaluation index Ps (step S51). Concerning this point, the control unit 2 can calculate the sedative management evaluation index Ps through the processes of steps S2 to S10 illustrated in FIG. 3.

Next, in step S52, the control unit 2 calculates the analgesic management evaluation index Pa after acquiring the heart rate data and/or the blood pressure data (step S53). Concerning this point, the control unit 2 can calculate the analgesic management evaluation index Pa through the processes of steps S21 to S28 illustrated in FIG. 5.

Next, in step S54, the control unit 2 calculates the muscle relaxation management evaluation index Pm after acquiring the TOF count value (step S55). Concerning this point, the control unit 2 can calculate the muscle relaxation management evaluation index Pm through the processes of steps S12 to S17 illustrated in FIG. 4.

Thereafter, the control unit 2 calculates and outputs the comprehensive anesthesia management evaluation index Pk based on the sedative management evaluation index Ps, the analgesic management evaluation index Pa, and the muscle relaxation management evaluation index Pm (step S56). For example, the control unit 2 may determine an average value of the sedative management evaluation index Ps, the analgesic management evaluation index Pa, and the muscle relaxation management evaluation index Pm to be the comprehensive anesthesia management evaluation index Pk (Pk=(Ps+Pa+Pm)/3). Further, the control unit 2 may determine a largest value or a smallest value among the sedative management evaluation index Ps, the analgesic management evaluation index Pa, and the muscle relaxation management evaluation index Pm to be the comprehensive anesthesia management evaluation index Pk. In this example, same or similarly, the skillfulness of the sedative management, the analgesic management, and the muscle relaxation management can be comprehensively and objectively digitalized and visualized through the comprehensive anesthesia management evaluation index Pk.

In order to achieve the processing apparatus 1 according to the present embodiment by software, the physiological information processing program may be incorporated in the storage device 3 or the ROM in advance. Alternatively, the physiological information processing program may be stored in a computer-readable storage medium such as a magnetic disk (for example, an HDD or a floppy disk), an optical disk (for example, a CD-ROM, a DVD-ROM, or a Blu-ray (registered trademark) disk), a magneto-optical disk (for example, an MO), or a flash memory (for example, an SD card, a USB memory, or an SSD). In this case, the physiological information processing program stored in the storage medium may be incorporated into the storage device 3. Further, the program incorporated in the storage device 3 may be loaded onto the RAM, and then the one or more processors may execute the program which is loaded onto the RAM. In this way, a physiological information processing method according to the present embodiment is executed by the processing apparatus 1.

The physiological information processing program may also be downloaded from a computer on a communication network via the network interface 4. In this case, same or similarly, the downloaded program may be incorporated into the storage device 3.

Although the embodiment of the presently disclosed subject matter have been described above, the technical scope of the presently disclosed subject matter should not be construed as being limited by the description of the embodiment. It is to be understood by those skilled in the art that the present embodiment is an example, and various modifications of the embodiment are possible within the scope of the invention described in the claims. The technical scope of the presently disclosed subject matter should be determined based on the scope of the invention described in the claims and the scope of equivalents thereof.

For example, although the acquisition time of the current BIS value is counted as the exclusion time when the SQI value is less than 80% according to the method of calculating the sedative management evaluation index illustrated in FIG. 3, the present embodiment is not limited thereto. Concerning this point, the processes of steps S3 and S4 may be omitted. That is, the process of step S5 may be executed after the process of step S2 is executed.

Although the time between the time tp corresponding to the maximum value of the heart rate waveform and the time tr corresponding to the rising point rising from the baseline by the predetermined rate is counted as the inappropriate management time according to the method of calculating the analgesic management evaluation index illustrated in FIG. 5, the present embodiment is not limited thereto. For example, the control unit 2 may specify a time tw when a predetermined time has elapsed from the time tp, and then count a time between the time tw and the time tr as the inappropriate management time. The time tw may be a time between a time tz, at which a value of the heart rate becomes $\gamma$% ($\gamma \leq 100$%) of the maximum value, and the time tp. In particular, the time tw may be a time between the time tz and the time tp when the value of the heart rate is equal to the baseline.

The time tw when the predetermined time has elapsed from the time tp may be selected by a medical worker. In this case, the control unit 2 may specify the time tw in accordance with an input operation from the medical worker and then count the time between the time tw and the time tr as the inappropriate management time.

What is claimed is:

1. A physiological information processing apparatus comprising:
a display;
a sensor interface connected to a plurality of sensors;
a processor; and
a memory configured to store a computer readable command, wherein,
when the computer readable command is executed by the processor, the physiological information processing apparatus is configured to:
acquire physiological information data of a subject to which an anesthetic is administered from the plurality of sensors;
specify, based on the physiological information data, at least one of an appropriate management time, which is a time during which anesthesia management is appropriately performed on the subject, and an inappropriate management time, which is a time during which the anesthesia management is not appropriately performed;
count, when the physiological information data satisfies a first condition, a time during which the physiological information data satisfying the first condition is acquired as an exclusion time;
calculate an anesthesia management evaluation index, which is an evaluation index for the anesthesia management, based on a ratio of the appropriate management time to a time obtained by subtracting the exclusion time from an operation time;
output the calculated anesthesia management evaluation index to the display; and
store the acquired physiological information data and the calculated anesthesia management evaluation index on the memory in association with the subject.

2. The physiological information processing apparatus according to claim 1, wherein
the physiological information data includes electroencephalogram data of the subject,
the anesthesia management includes sedative management of the subject, and
the anesthesia management evaluation index includes a sedative management evaluation index that is an evaluation index for the sedative management.

3. The physiological information processing apparatus according to claim 2, wherein the physiological information processing apparatus is configured to:
specify, based on the electroencephalogram data, a BIS value indicating a sedative effect of the subject;
count, when the BIS value satisfies a second condition, a time during which the BIS value satisfying the second condition is acquired as the appropriate management time;
count, when the BIS value does not satisfy the second condition, a time during which the BIS value that does not satisfy the second condition is acquired as the inappropriate management time; and
calculate the sedative management evaluation index based on the appropriate management time and the operation time.

4. The physiological information processing apparatus according to claim 1, wherein
the physiological information data includes stimulus-response data indicating a stimulus-response of the subject,
the anesthesia management includes muscle relaxation management of the subject, and
the anesthesia management evaluation index includes a muscle relaxation management evaluation index that is an evaluation index for the muscle relaxation management of the subject.

5. The physiological information processing apparatus according to claim 4, wherein the physiological information processing apparatus is configured to:
count, when the stimulus-response data satisfies a third condition, a time during which the stimulus-response data satisfying the third condition is acquired as the appropriate management time;

count, when the stimulus-response data does not satisfy the third condition, a time during which the stimulus-response data that does not satisfy the third condition is acquired as the inappropriate management time; and calculate the muscle relaxation management evaluation index based on the appropriate management time and the inappropriate management time.

6. The physiological information processing apparatus according to claim 1, wherein the physiological information data includes pain reaction data indicating a pain reaction of the subject, the anesthesia management includes analgesic management of the subject, and the anesthesia management evaluation index includes an analgesic management evaluation index that is an evaluation index for the analgesic management.

7. The physiological information processing apparatus according to claim 6, wherein the physiological information processing apparatus is configured to:

specify a first time corresponding to a maximum value of a waveform of the pain reaction data;

specify a second time corresponding to a rising point of the waveform;

specify the inappropriate management time based on the first time and the second time;

specify the appropriate management time based on the inappropriate management time and the operation time; and calculate the analgesic management evaluation index based on the appropriate management time and the operation time.

8. The physiological information processing apparatus according to claim 7, wherein the rising point is a point that rises by a predetermined rate from a baseline indicating an average value of the pain reaction data in a time zone before the second time.

9. The physiological information processing apparatus according to claim 6, wherein the pain reaction data includes at least one of blood pressure data indicating a change over time in blood pressure of the subject and heart rate data indicating a change over time in heart rate of the subject.

10. The physiological information processing apparatus according to claim 9, wherein the physiological information processing apparatus is configured to:

acquire the blood pressure data and the heart rate data;

specify an inappropriate management time associated with the blood pressure data and specify an inappropriate management time associated with the heart rate data; and specify the appropriate management time based on the inappropriate management time associated with the blood pressure data, the inappropriate management time associated with the heart rate data, and the operation time.

11. The physiological information processing apparatus according to claim 1, wherein the plurality of sensors comprise:

an electroencephalogram sensor;

a stimulus-response sensor; and a pain reaction sensor.

12. The physiological information processing apparatus according to claim 1, wherein the physiological information processing apparatus is further configured to:

acquire the physiological information data of the subject to which the anesthetic is administered from the plurality of sensors repeatedly in a preset time interval.

13. A physiological information processing method executed by a computer, comprising:

acquiring physiological information data from a plurality of sensors connected to a subject to which an anesthetic is administered;

specifying, based on the physiological information data, at least one of an appropriate management time, which is a time during which anesthesia management is appropriately performed on the subject, and an inappropriate management time, which is a time during which the anesthesia management is not appropriately performed;

counting, when the physiological information data satisfies a first condition, a time during which the physiological information data satisfying the first condition is acquired as an exclusion time;

calculating an anesthesia management evaluation index, which is an evaluation index for the anesthesia management, based on a ratio of the appropriate management time to a time obtained by subtracting the exclusion time from an operation;

outputting the calculated anesthesia management evaluation index to a display; and storing the acquired physiological information data and the calculated anesthesia management evaluation index on the memory in association with the subject.

14. The physiological information processing method of claim 13, wherein the physiological information data is acquired from the plurality of sensors repeatedly in a preset time interval.

15. A non-transitory computer-readable medium storing a program configured to cause a computer to execute the physiological information processing method according to claim 13.

* * * * *